US008486641B2

(12) United States Patent
Karin

(10) Patent No.: US 8,486,641 B2
(45) Date of Patent: *Jul. 16, 2013

(54) COMPOSITIONS AND METHODS FOR DIAGNOSING AND TREATING PROSTATE CANCER

(75) Inventor: Nathan Karin, Haifa (IL)

(73) Assignee: Rappaport Family Institute for Research in the Medical Sciences, Haifa (IL)

( * ) Notice: Subject to any disclaimer, the term of this patent is extended or adjusted under 35 U.S.C. 154(b) by 206 days.

This patent is subject to a terminal disclaimer.

(21) Appl. No.: 12/785,515

(22) Filed: May 24, 2010

(65) Prior Publication Data

US 2010/0261210 A1   Oct. 14, 2010

Related U.S. Application Data

(63) Continuation of application No. 10/548,605, filed as application No. PCT/IL2004/000240 on Mar. 14, 2004, now Pat. No. 7,749,714.

(60) Provisional application No. 60/534,111, filed on Jan. 5, 2004, provisional application No. 60/525,135, filed on Nov. 28, 2003, provisional application No. 60/453,514, filed on Mar. 12, 2003, provisional application No. 60/453,515, filed on Mar. 12, 2003.

(51) Int. Cl.
G01N 33/53 (2006.01)

(52) U.S. Cl.
USPC .......................................................... 435/7.1

(58) Field of Classification Search
None
See application file for complete search history.

(56) References Cited

U.S. PATENT DOCUMENTS

| | | | |
|---|---|---|---|
| 5,459,128 A | 10/1995 | Rollins et al. | |
| 5,888,511 A | 3/1999 | Skurkovich et al. | |
| 6,087,385 A | 7/2000 | Pershadsingh et al. | |
| 6,316,420 B1 | 11/2001 | Karin et al. | |
| 6,420,346 B1 | 7/2002 | Karin | |
| 6,429,289 B1 | 8/2002 | Krieger et al. | |
| 7,245,748 B2 | 7/2007 | Degani et al. | |
| 7,345,910 B2 | 3/2008 | Tsukamoto et al. | |
| 7,417,037 B2 | 8/2008 | Harty | |
| 7,465,444 B2 | 12/2008 | Watanabe | |
| 7,749,714 B2 | 7/2010 | Karin | |
| 8,017,113 B2 | 9/2011 | Karin | |
| 2002/0086483 A1 | 7/2002 | Kim et al. | |
| 2002/0090379 A1 | 7/2002 | Mouritsen et al. | |
| 2004/0047861 A1 | 3/2004 | Kehrel et al. | |
| 2004/0052790 A1 | 3/2004 | Skurkovich et al. | |
| 2004/0086483 A1 | 5/2004 | Karin | |
| 2006/0035834 A1 | 2/2006 | Karin | |
| 2006/0193863 A1 | 8/2006 | Karin | |
| 2011/0287030 A1 | 11/2011 | Karin et al. | |
| 2011/0287457 A1 | 11/2011 | Karin et al. | |

FOREIGN PATENT DOCUMENTS

| | | |
|---|---|---|
| EP | 1411848 | 4/2004 |
| EP | 1601374 | 12/2005 |
| EP | 1601682 | 12/2005 |
| EP | 1924605 | 5/2008 |
| WO | WO 95/05600 | 2/1995 |
| WO | WO 96/00288 | 1/1996 |
| WO | WO 99/11288 | 3/1999 |
| WO | WO 00/06203 | 2/2000 |
| WO | WO 01/57056 | 8/2001 |
| WO | WO 01/89565 | 11/2001 |
| WO | WO 02/16549 | 2/2002 |
| WO | WO 03/002009 | 1/2003 |
| WO | WO 2004/016769 | 2/2004 |
| WO | WO 2004/041179 | 5/2004 |
| WO | WO 2004/080273 | 9/2004 |
| WO | WO 2004/080385 | 9/2004 |
| WO | WO 2005/025613 | 3/2005 |
| WO | WO 2007/031996 | 3/2007 |

OTHER PUBLICATIONS

Sylvester et al., J. Immunol., 1993, 151(6): 3292-3298.*
Response Dated Oct. 27, 2011 to Official Action of Sep. 28, 2011 From the US Patent and Trademark Office Re. U.S. Appl. No. 13/205,665.
Response Dated Oct. 31, 2011 to Official Action of Jul. 7, 2011 From the US Patent and Trademark Office Re.: U.S. Appl. No. 11/991,711.
Examination Report Dated Apr. 8, 2010 From the Instituto Mexicano de la Propriedad Industrial Re. Application No. MX/a/2008/003437 and Its Summary in English.
Official Action Dated Jul. 7, 2011 From the US Patent and Trademark Office Re.: U.S. Appl. No. 11/991,711.
Office Action Dated Jul. 27, 2010 From the Israel Patent Office Re. Application No. 190101 and Its Translation Into English.
Response Dated Sep. 29, 2010 to Official Action of Mar. 29, 2010 From the US Patent and Trademark Office Re.: U.S. Appl. No. 11/222,745.
Response Dated Mar. 21, 2011 to Official Action of Dec. 21, 2010 From the US Patent and Trademark Office Re.: U.S. Appl. No. 11/222,745.
Notice of Allowance Dated Apr. 4, 2011 From the US Patent and Trademark Office Re.: U.S. Appl. No. 11/222,745.
Official Action Dated Nov. 6, 2000 From the US Patent and Trademark Office Re.: U.S. Appl. No. 09/498,625.
Response Dated Oct. 27, 2011 to Official Action of Sep. 27, 2011 From the US Patent and Trademark Office Re. U.S. Appl. No. 13/205,668.
Communication Pursuant to Article 101(1) and Rule 82(1) EPC Dated Feb. 11, 2011 From the European Patent Office Re.: Application No. 04720545.5.
Official Action Dated Dec. 22, 2011 From the US Patent and Trademark Office Re. U.S. Appl. No. 13/205,668.
Official Action Dated Dec. 29, 2011 From the US Patent and Trademark Office Re. U.S. Appl. No. 13/205,665.

(Continued)

Primary Examiner — Hong Sang

(57) ABSTRACT

A method of diagnosing and determining a predisposition to prostate cancer is provided. The method comprising determining levels of MCP-1 antibodies and PSA in a sample of a subject and comparing to the level in healthy male controls, thereby diagnosing and determining a predisposition to the prostate cancer in the subject.

11 Claims, 9 Drawing Sheets

OTHER PUBLICATIONS

Abaza et al. "Effects of Amino Acid Substitutions Outside an Antigenic Site on Protein Binding to Monoclonal Antibodies of Predetermined Specificity Obtained by Peptide Immunization: Demonstration With Region 94-100 (Antigenic Site 3) of Myoglobin", Journal of Protein Chemistry, 11(5): 433-444, 1992.

Colman "Effects of Amino Acid Sequence Changes on Antibody-Antigen Interactions", Research in Immunology, 145(1): 33-36, 1994.

Lederman et al. "A Single Amino Acid Substitution in a Common African Allele of the CD4 Molecule Ablates Binding of the Monoclonal Antibody, OKTa", Molecular Immunology, 28(11): 1171-1181, 1991.

Ngo et al. "Computational Complexicity, Protein Structure Prediction, and the Levinthal Paradox", The Protein Folding Problem and Tertiary Structure Prediction, Chap.14: 491-495, 1994.

Office Action Dated Dec. 26, 2011 From the Israel Patent Office Re. Application No. 190101 and Its Translation Into English.

Communication Pursuant to Rule 82(2) EPC Dated Dec. 27, 2011 From the European Patent Office Re.: Application No. 04720545.5.

Communication Pursuant to Article 94(3) EPC Dated Nov. 27, 2008 From the European Patent Office Re.: Application No. 06796079.9.

Response Dated Nov. 20, 2007 to Communication Pursuant to Article 96(2) EPC of Nov. 9, 2007 From the European Patent Office Re.: Application No. 04720550.5.

Communication of a Notice of Opposition Dated Jul. 6, 2009 From the European Patent Office Re.: Application No. 04720545.5.

Communication Pursuant to Article 94(3) EPC Dated Jun. 16, 2009 From the European Patent Office Re.: Application No. 06796079.9.

Communication Pursuant to Article 96(2) EPC Dated Apr. 5, 2007 From the European Patent Office Re.: Application No. 04720550.5.

Communication Pursuant to Article 96(2) EPC Dated Apr. 10, 2007 From the European Patent Office Re.: Application No. 04720545.5.

Examination Report Dated Mar. 4, 2010 From the Intellectual Property Office of New Zealand Re.: Application No. 566927.

International Preliminary Report on Patentability Dated Feb. 3, 2010 From the International Preliminary Examining Authority Re.: Application No. PCT/IL01/00117.

International Preliminary Report on Patentability Dated May 5, 2006 From the International Preliminary Examining Authority Re.: Application No. PCT/IL04/00240.

International Preliminary Report on Patentability Dated Aug. 8, 2007 From the International Preliminary Examining Authority Re.: Application No. PCT/IL2006/001059.

International Search Report Dated Feb. 1, 2007 From the International Searching Authority Re.: Application No. PCT/IL2006/001059.

International Search Report Dated May 3, 2001 From the International Searching Authority Re.: Application No. PCT/IL01/00117.

International Search Report Dated Jun. 28, 2005 From the International Searching Authority Re.: Application No. PCT/IL04/00240.

International Search Report Dated Jun. 29, 2005 From the International Searching Authority Re.: Application No. PCT/IL04/00241.

Notice of Allowance Dated Feb. 22, 2010 From the US Patent and Trademark Office Re.: U.S. Appl. No. 10/548,605.

Office Action Dated Dec. 10, 2008 From the Israeli Patent Office Re.: Application No. 170793 and Its Translation Into English.

Office Action Dated Nov. 11, 2009 From the Israel Patent Office Re.: Application No. 170819 and Its Translation Into English.

Office Action Dated Dec. 14, 2008 From the Israeli Patent Office Re.: Application No. 170819 and Its Translation Into English.

Office Action Dated Nov. 16, 2009 From the Israel Patent Office Re.: Application No. 170793 and Its Translation Into English.

Official Action Dated Sep. 1, 2009 From the US Patent and Trademark Office Re.: U.S. Appl. No. 10/548,605.

Official Action Dated May 2, 2007 From the US Patent and Trademark Office Re.: U.S. Appl. No. 10/548,605.

Official Action Dated Jun. 4, 2009 From the US Patent and Trademark Office Re.: U.S. Appl. No. 11/222,745.

Official Action Dated Mar. 4, 2009 From the US Patent and Trademark Office Re.: U.S. Appl. No. 10/548,605.

Official Action Dated Feb. 6, 2008 From the US Patent and Trademark Office Re.: U.S. Appl. No. 10/548,605.

Official Action Dated Nov. 14, 2008 From the US Patent and Trademark Office Re.: U.S. Appl. No. 10/548,605.

Official Action Dated Oct. 17, 2008 From the US Patent and Trademark Office Re.: U.S. Appl. No. 11/222,745.

Official Action Dated Jul. 25, 2007 From the US Patent and Trademark Officie Re.: U.S. Appl. No. 10/548,605.

Official Action Dated Mar. 29, 2010 From the US Patent and Trademark Office Re.: U.S. Appl. No. 11/222,745.

Official Action Dated May 30, 2008 From the US Patent and Trademark Office Re.: U.S. Appl. No. 10/548,605.

Requisition by the Examiner Dated Nov. 24, 2008 From the Canadian Intellectual Property Office Re.: Application No. 2,451,702.

Response Dated Dec. 1, 2009 to Official Action of Sep. 1, 2009 From the US Patent and Trademark Office Re.: U.S. Appl. No. 10/548,605.

Response Dated Mar. 7, 2010 to Office Action of Nov. 16, 2009 From the Israel Patent Office Re.: Application No. 170793.

Response Dated Feb. 15, 2010 to Communication of a Notice of Opposition of Jul. 6, 2009 From the European Patent Office Re.: Application No. 04720545.5.

Response Dated Feb. 27, 2009 to Official Action of Oct. 17, 2008 From the US Patent and Trademark Office Re.: U.S. Appl. No. 11/222,745.

Supplementary European Search Report Dated May 23, 2006 From the European Patent Office Re.: Application No. 04720550.5.

Supplementary European Search Report Dated May 29, 2006 From the European Patent Office Re.: 04720545.5.

Written Opinion Dated Feb. 1, 2007 From the International Searching Authority Re.: Application No. PCT/IL2006/001059.

Written Opinion Dated Jun. 28, 2005 From the International Searching Authority Re.: Applicaiton No. PCT/IL04/00240.

Written Opinion Dated Jun. 29, 2005 From the International Searching Authority Re.: Application No. PCT/IL04/00241.

Bottazzi et al. "A Chemoattractant Expressed in Human Sarcoma Cells (Tumor-Derived Chemotactic Factor, TDCF) Is Identical to Monocyte Chemoattractant Protein-1/Monocyte Chemotactic and Activating Factor (MCP-1/MCAF)", International Journal of Cancer, 45: 795-797, 19 90.

Braciak et al. "Recombinant Adenovirus-mRANTES Gene Transfer Into B16 Mouse Melanoma Cells Reduces Tumorgenicity In Vivo", The FASEB Journal, 8(4): Abstract 1159, 1994.

Brennan et al. "Cytokines in Autoimmunity", Current Opinion in Immunology, 8(6): 872-877, 1996.

Cao et al. "Complete Regression of Established Murine Hepatocellular Carcinoma by In Vivo Tumor Necrosis Factor α Gene Transfer", Gastroenterology, 112: 501-510, 1997.

Chetcuti et al. "Identification of Differentially Expressed Genes in Organ-Confined Prostate Cancer by Gene Expression Array", The Prostate, 47: 132-140, 2001. Fig.5, Table I.

Cho "The Genetics and Immunopathogenesis of Inflammatory Bowel Disease", Nature Reviews: Immunology, 8(6): 458-466, 2008.

Colozza et al. "Proliferative Markers as Prognostic and Predictive Tools in Early Breast Cancer: Where Are We Now?", Annals of Oncology, 16: 1723-1739, 2005.

Cruse et al. "Antibodies", Illustrated Dictionary of Immunology, CRC Press, p. 18-19, 1995.

Desbaillets et al. "Human Astrocytomas and Glioblastomas Express Monocyte Chemoattractant Protein-1 (MCP-1) In Vivo and In Vitro", International Journal of Cancer, 58: 240-247, 1994.

Dohi et al. "Hapten-Induced Colitis Is Associated With Colonic Patch Hypertrophy and T Helper Cell 2-Type Responses", Journal of Experimental Medicine, 189(8): 1169-1179, Apr. 19, 1999.

Feldmann et al. "Role of Cytokines in Rheumatoid", Annual Reviews in Immunology, 14: 397-440, 1996.

Graves et al. "Monocyte Chemotactic Proteins From Human Tumor Cells", Biochemical Pharmacology, 47(3): 333-337, 1991.

Hayashida et al. "Lectin-Like Oxidized LDL Receptor-1 (LOX-1) Supports Adhesion of Mononuclear Leukocytes and A Monocyte-Like Cell Line THP-1 Cells Under Static and Flow Conditions", FEBS Letters, 511(1-3): 133-138, 2002. Introduction, Abstract.

Isik et al. "Monocyte Chemoattractant Protein-1 mRNA Expression in Hemangiomas and Vascular Malformations", Journal of Surgical Research, 61: 71-76, 1996.

Janciauskiene et al. "C-Terminal of ?1-Antitrypsin Activates Human Monocytes to a Pro-Inflammatory State Through Interactions With the CD36 Scavenger Receptor and LDL Receptor", Atherosclerosis, 158(1): 41-51, 2001.

Jiang et al. "Post-Translational Modification of A Monocyte-Specific Chemoattractant Synthesized by Glioma, Osteosarcoma, and Vascular Smooth Muscle Cells", The Journal of Biological Chemistry, 265(30): 18318-18321, 1990.

Karin "Gene Therapy for T Cell-Mediated Autoimmunity: Teaching the Immune System How to Restrain Its Own Harmful Activities by Targeted DNA Vaccines", IMAJ Journal, 2(Suppl.): 63-68, 2000.

Kasama et al. "Interleukin-10 Expression and Chemokine Regulation During the Evolution of Murine Type II Collagen-Induced Arthritis", Journal of Clinical Investigation, 95: 2868-2876, 1995.

Kawahito et al. "15-Deoxy-Δ12,14-PGJ2 Induces Synoviocyte Apoptosis and Suppresses Adjuvant-Induced Arthritis in Rats", Journal of Clinical Investigation, 106(2): 189-197, 2000.

Krajewska et al. "Expression of BAG-I Protein Correlates With Aggressive Behavior of Prostate Cancers", The Prostate, 66: 801-810, 2006.

Leonard "Plasma Chemokine and Chemokine-Autoantibody Complexes in Health and Disease", Methods: A Companion to Methods in Enzymology, 10: 150-157, 1996.

Leung et al. "Monocyte Chemoattractant Protein-1 Expression and Macrophage Infiltration in Gliomas", Acta Neuropathologica, 93: 518-527, 1997.

Lubberts et al. "Adenoviral Vector-Mediated Overexpression of IL-4 in the Knee Joint of Mice With Collagen-Induced Arthritis Prevents Cartilage Destruction", Journal of Immunology, 163: 4546-4556, 1999. Abstract.

Mazzucchelli et al. "Monocyte Chemoattractant Protein-1 Gene Expression in Prostatic Hyperplasia and Prostate Adenocarcinoma", American Journal of Pathology, 149(2): 501-509, 1996. Abstract.

Momoi et al. "Inhibition of Monocyte Chemoattractant Protein-1 Expression in Cytokine-Treated Human Lung Epithelial Cells by Thiazolidinedione", Chest, 120(4): 1293-1300, 2001. Abstract.

Moore et al. "Distinct CXC Chemokines Mediate Tumorigenicity of Prostate Cancer Cells", American Journal of Pathology, 154(5): 1503-1512, 1999.

Murao et al. "Thiazolidinedione Inhibits the Production of Monocyte Chemoattractant Protein-1 in Cytokine-Treated Human Vascular Endothelial Cells", FEBS Letters, 454(1-2): 27-30, 1999. Abstract.

Negus et al. "The Detection and Localization of Monocyte Chemoattractant Protein-1 (MCP-1) in Human Ovarian Cancer", Journal of Clinical Investigation, 95: 2391-2396, 1995.

Nesbit et al. "Low-Level Monocyte Chemoattractant Protein-1 Stimulation of Monocytes Leads to Tumor Formation in Nontumorigenic Melanoma Cells", The Journal of Immunology: 6483-6490, 2001.

Podgaec et al. "Endometriosis: An Inflammatory Disease With A Th2 Immune Response Component", Human Reproduction, 22(5): 1373-1379, 2007.

Rudikoff et al. "Single Amino Acid Substitution Altering Antigen-Binding Specificity", Proc. Natl. Acad. Sci. USA, 79(6): 1979-1983, 1982.

Scarselli et al. "The Human Scavenger Receptor Class B Type I is a Novel Candidate Receptor for the Hepatitis C Virus", The EMBO Journal, 21(19): 5017-5025, 2002. p. 5020, r-h Col., Lines 35-56, p. 5023, l-h Col., Lines 7-26.

Selvan et al. "Expression of Multiple Chemokine Genes by Human Mast Cells Leukemia", The Journal of Biological Chemistry, 269(19): 13893-13898, 1994.

Sylvester et al. "Neutrophil Attractant Protein-1 and Monocyte Chemoattractant Protein-1 in Human Serum. Effects of Intravenous Lipopolysaccharide on Free Attractants, Specific IgG Autoantibodies and Immune Complexes", The Journal of Immunology, 151(6): 3292-3298, Sep. 15, 1993.

Tang et al. "Expression of BAG-1 in Invasive Breast Carcinomas", Journal of Clinical Oncology, 17(6): 1710-1719, Jun. 1999.

Temel et al. "Scavenger Receptor Class B, Type I (SR-BI) Is the Major Route for the Delivery of High Density Lipoprotein Cholesterol to the Steroidgenic Pathway in Cultured Mouse Adrenocortical Cells", Proc. Natl. Acad. Sci. USA, 94: 13600-13605, 1997. Abstract.

Turner et al. "BAG-1: A Novel Biomarker Predicting Long-Term Survival in Early-Stage Breast Cancer", Journal of Clinical Oncology, 19(4): 992-1000, Feb. 15, 2001.

Van der Laan et al. "Regulation and Functional Involvement of Macrophage Scavenger Receptor MARCO in Clearence of Bacteria In Vivo", The Journal of Immunology, XP002380142, 162(2): 939-947, 1999.

Wildbaum et al. "A Targeted DNA Vaccine Augments the Natural Immune Response to Self TNF-Alpha and Suppresses Ongoing Adjuvant Arthritis", Journal of Immunolgy, 165(10): 5860-5866, 2000. p. 5860, Claims 1-10.

Wildbaum et al. "Augmentation of Natural Immunity to A Proinflammatory Cytokine (TNF-Alpha) by Targeted DNA Vaccine Confers Long-Lasting Resistance to Experimental Autoimmune Encephalomyelitis", Gene Therapy, 6: 1128-1138, 1999.

Wirger et al. "Plasma Levels of Monocyte Chemoattractant Protein-1 (MCP-1) in Patients With Metastatic Urological Cancers", Urological Research, 25(1): 92, 1997. Abstract p. 3.4.

Yoshimura et al. "Production and Characterization of Mouse Monoclonal Antibodies Against Human Monocyte Chemoattractant Protein-1", The Journal of Immunology, 147(7): 2229-2233, 1991.

Youssef et al. "Long-Lasting Protective Immunity to Experimental Autoimmune Encephalomyelitis Following Vaccination With Naked DNA Encoding C—C Chemokines", The Journal of Immunology, p. 3870-3879, 1998.

Youssef et al. "Prevention of Experimental Autoimmune Encephalomyelitis by MIP-1 α and MCP-1 Naked DNA", Journal of Autoimmunity, 13: 21-29, 1999.

Official Action Dated Sep. 27, 2011 From the US Patent and Trademark Office Re. U.S. Appl. No. 13/205,668.

Official Action Dated Sep. 28, 2011 From the US Patent and Trademark Office Re. U.S. Appl. No. 13/205,665.

Scarselli et al. "The Human Scavenger Receptor Class B Type I is a Novel Candidate Receptor for the Hepatitis C Virus", The EMBO Journal, 21(19): 5017-5025, 2002. p. 5020, r-h Col., Lines 35-56, p. 5023, l-h Col., Lines 7-26.

Office Action Dated May 5, 2011 From the Israel Patent Office Re. Application No. 207419 and Its Translation Into English.

Official Action Dated Mar. 5, 2012 From the US Patent and Trademark Office Re.: U.S. Appl. No. 11/991,711.

Communication Pursuant to Article 96(2) EPC Dated Feb. 8, 2006 From the European Patent Office Re. Application No. 01904289.4.

International Search Report Dated Jan. 25, 2005 From the International Searching Authority Re. Application No. PCT/IL04/00243.

Office Action Dated Aug. 22, 2010 From the Israel Patent Office Re. Application No. 207419.

Official Action Dated Dec. 21, 2010 From the US Patent and Trademark Office Re.: U.S. Appl. No. 11/222,745.

Response Dated Dec. 19, 2010 to Office Action of Aug. 22, 2010 From the Israel Patent Office Re. Application No. 207419.

Response Dated Nov. 28, 2010 to Office Action of Jul. 27, 2010 From the Israel Patent Office Re. Application No. 190101.

Response Dated Jan. 24, 2011 to Summons to Attend Oral Proceedings Pursuant to Rule 115(1) EPC of Oct. 12, 2010 From the European Patent Office Re. Application No. 04720545.5.

Summons to Attend Oral Proceedings Pursuant to Rule 115(1) EPC Dated Oct. 12, 2010 From the European Patent Office Re. Application No. 04720545.5.

Barter et al. "HDL Cholesterol, Very Low Levels of LDL Cholesterol, and Cardiovascular Events", The New England Journal of Medicine, 357(13): 1301-1310, Sep. 27, 2007.

Bocharov et al. "Synthetic Amphipathic Alpha-Helical Peptides, Mimics of Exchangeable Apolipoproteins, Block LPS Uptake and the Lipopolysaccharide-Induced Proinflammatory Cytokine Response in THP-1 Monocyte Cells", Circulation, Supplement II, 106(19): II-84, Abstract 425, Nov. 5, 2002.

Gordon et al. "High-Density Lipoprotein Cholesterol and Cardiovascular Disease. Four Prospective American Studies", Circulation, 79: 8-15, 1989.

Imachi et al. "Expression of Human Scavenger Receptor B1 on and in Human Platelets", Arterisclerosis, Thrombosis, and Vascular Biology, 23(5): 898-904, May 1, 2003.

Imachi et al. "Reduction of CLA-1 Expression on Human Platelet in the Patients With Atherosclerotic Disease and Diabetes Mellitus", Bunshi Tonyobyogaku, 10: 47-51, Dec. 1999. ACS on STN, HCAPLUS, AN 2000:540461, Accession No. 134:176698, Aug. 8, 2000.

Sriram et al. "Experimental Allergic Encephalomyelitis: A Misleading Model of Multiple Sclerosis", Annals of Neurology, 58(6): 939-945, Dec. 2005.

Tandon et al. "Anti-CD36 Antibodies in Thrombotic Thrombocytopenic Purpura", British Journal of Haematology, 88: 816-825, Dec. 1994.

Official Action Dated Apr. 23, 2012 From the US Patent and Trademark Office Re. U.S. Appl. No. 13/205,668.

Chen et al. "Anti-Class A Scavanger Receptor Autoantibodies From Systemic Lupus erythematosus Patients Impair Phagocytic Clearance of Apoptotic Cells by Macrophages In Vitro", Arthritis Research and Therapy, 13: R1-R9, 2011.

Notice of Allowance Dated Oct. 2, 2012 From the US Patent and Trademark Office Re. U.S. Appl. No. 13/205,665.

Official Action Dated Sep. 21, 2012 From the US Patent and Trademark Office Re.: U.S. Appl. No. 11/991,711.

Official Action Dated Sep. 25, 2012 From the US Patent and Trademark Office Re. U.S. Appl. No. 13/205,668.

Office Action Dated Dec. 11, 2012 From the Israel Patent Office Re. Application No. 218580 and Its Translation Into English.

Office Action Dated Dec. 11, 2012 From the Israeli Patent Office Re.: Application No. 170819 and Its Translation Into English.

* cited by examiner

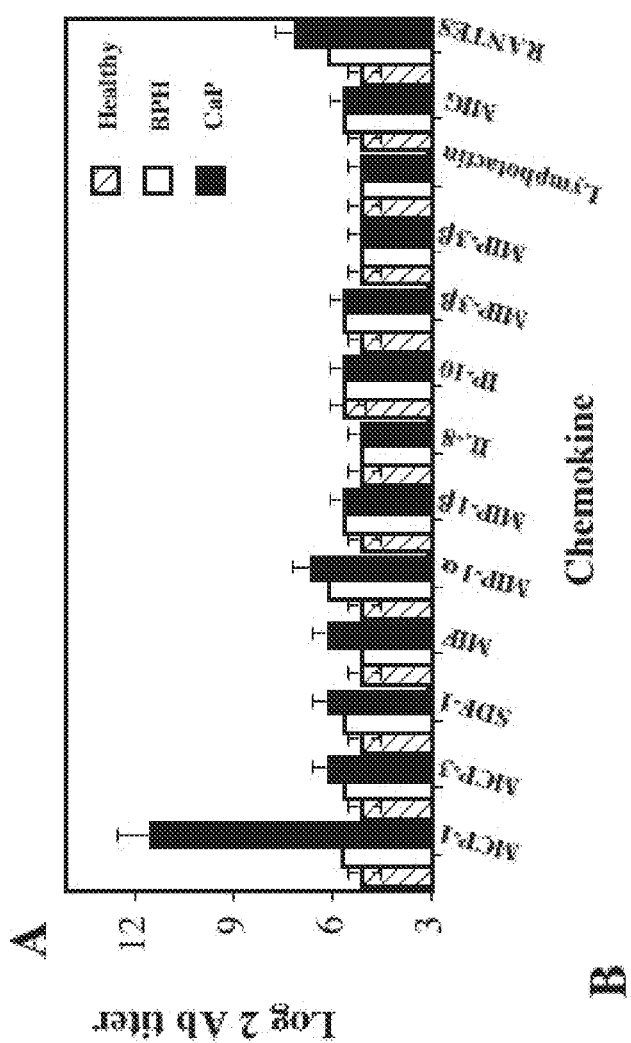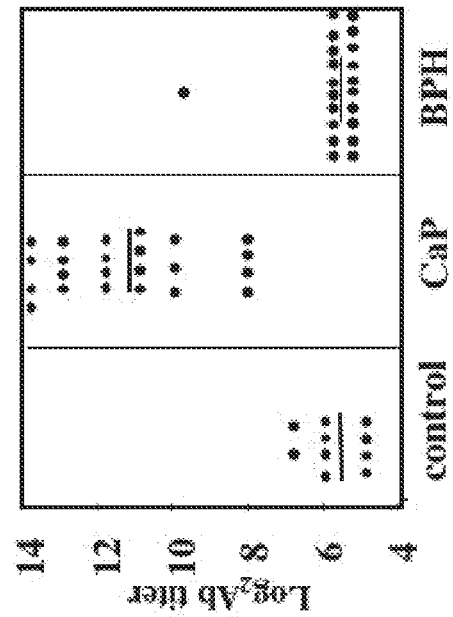

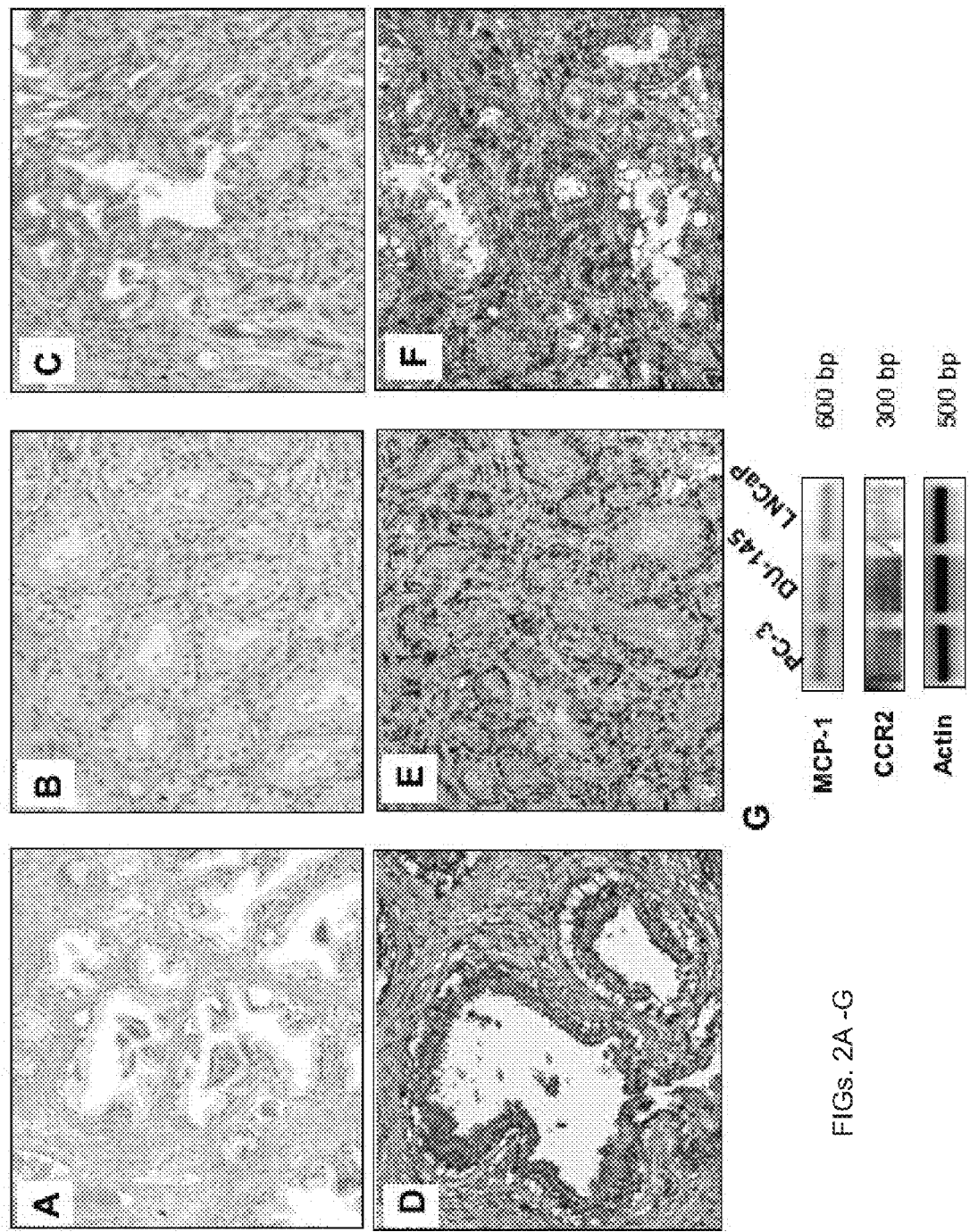
FIGs. 2A-G

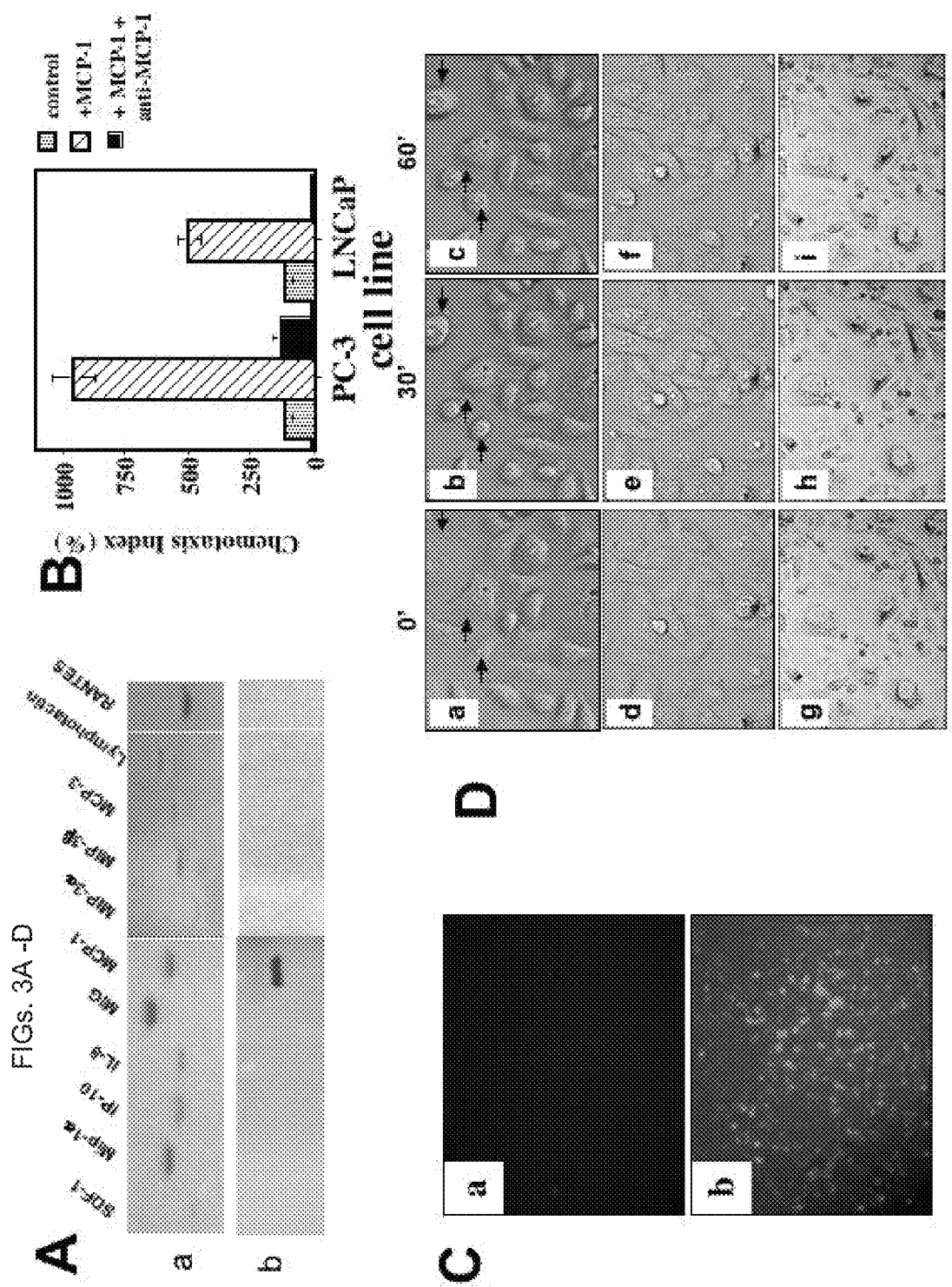
FIGs. 3A-D

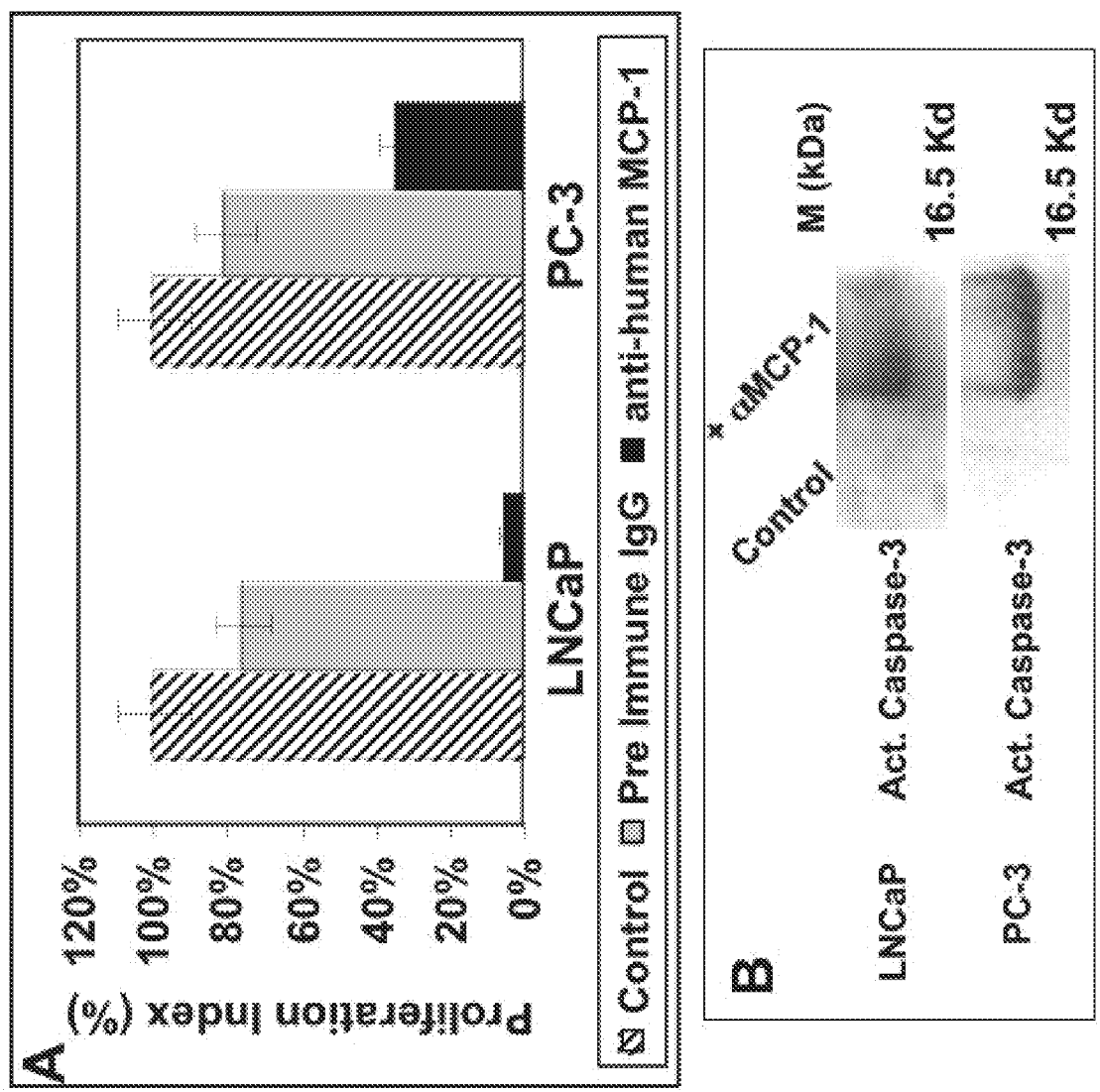
FIGs. 4 A-B

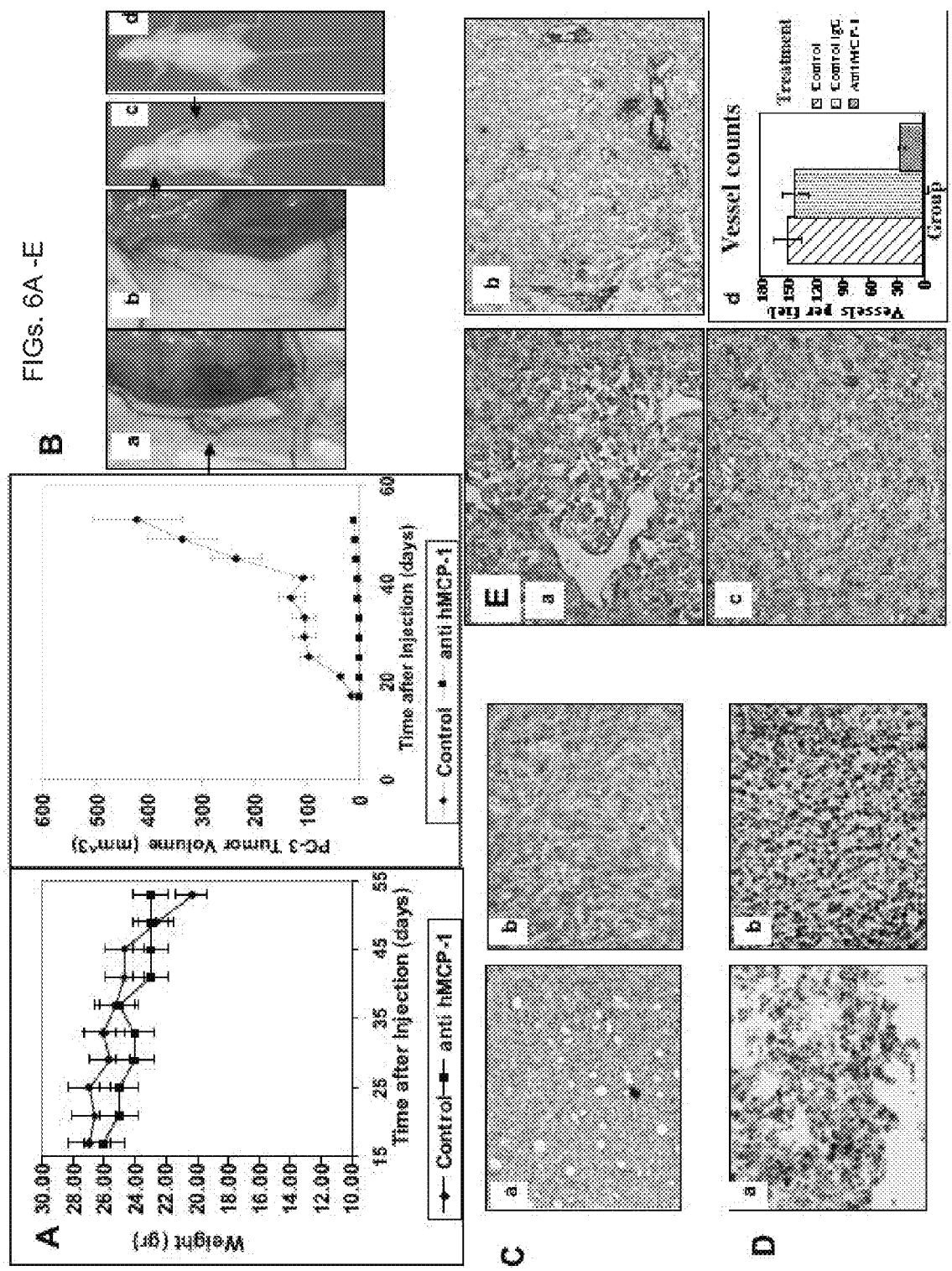
FIGs. 6A-E

COMPOSITIONS AND METHODS FOR DIAGNOSING AND TREATING PROSTATE CANCER

RELATED PATENT APPLICATION

This application is a continuation of U.S. patent application Ser. No. 10/548,605 filed Sep. 12, 2005, which is a National Phase of PCT Patent Application No. PCT/IL2004/000240 having International Filing Date of Mar. 14, 2004, which claims the benefit of U.S. Provisional Patent Application Nos. 60/534,111 filed Jan. 5, 2004, 60/525,135 filed Nov. 28, 2003, 60/453,515 filed Mar. 12, 2003, and 60/453,514 filed Mar. 12, 2003.

The contents of all of the above applications are incorporated by reference as if fully set forth herein.

FIELD AND BACKGROUND OF THE INVENTION

The present invention relates to compositions and methods for diagnosing and treating cancer. More particularly, the present invention relates to the use of MCP-1 inhibitors in treating prostate cancer and to methods of diagnosing prostate cancer via detection of MCP-1 expression or activity.

Cancer of the prostate (CaP) is the most common cancer in American males, and the second cause of cancer-related mortality[22,23]. Adenocarcinoma of the prostate attacks mainly men older than 50 years, and the high mortality rate is principally due to the spread of malignant cells to different tissues, a process called metastasis. Incidence and death rates from metastatic processes continue to grow substantially since 1980, with the aging population, hence the importance of early detection and treatment of the disease. The precise etiology of prostate cancer is unknown, although there is some hormonal relationship and possibly a multi-step process involved in the transformation of a benign epithelial cell to adenocarcinoma.

Chemokines are a group of small (~8-14 kDa), mostly basic, structurally related molecules that regulate cell trafficking of various types of leukocytes through interactions with a subset of seven-transmembrane, G protein-coupled receptors[1].

The present inventor have previously shown that the immune system can selectively generate autoimmunity to chemokines and other proinflammatory mediators when such a response is beneficial for the host[2-9]. For example, patients suffering from rheumatoid arthritis (RA) but not osteoarthritis (OA) have significant levels of autoantibodies directed to TNF-α, and therapies that neutralize the function of TNF-α suppress RA but not OA[2]. Selective amplification of these beneficial antibodies by targeted DNA vaccines provided protective immunity in experimental models[2-9]. Interestingly, to date, no evidence correlating generation of autoimmunity to chemokines and cancer diseases exists.

Primary tumor growth, invasion and metastasis to distant organs are dependent on a highly orchestrated series of events. These events include cellular transformation, establishment of a pro-angiogenic environment, local tumor cell growth, invasion through the extracellular matrix (ECM) and vascular basement membrane and entry into the circulation, and finally, a nonrandom tumor-cell homing and metastasis to distant organs. It has been suggested that chemokines that direct leukocyte migration to target organs are also involved in tumor invasion[10-12], angiogenesis[13-15] and survival[16]. However, the significance of their role in the dynamics of tumor biology is still unclear.

MCP-1 (Monocyte chemoatractant protein-1, CCL2) is a CC chemokine which functions in attracting monocytes to a target tissue via chemotaxis; at the site of inflammation, MCP-1 further functions in activating monocytes to mature into macrophages[17]. Various cell types including monocytes, fibroblasts, endothelium, smooth muscle cells, and keratinocytes produce MCP-1[17]. In addition to monocytes, MCP-1 can also attract T lymphocytes, neutrophils and NK cells, all of which express the CCR2 receptor. It is well established that MCP-1 plays a pivotal role in autoimmunity[8,9,18-21]. Specifically, the present inventors have previously shown that during T cell mediated autoimmune diseases, the immune system generates a beneficial autoimmune response to MCP-1 and that amplification thereof rapidly suppresses these diseases[8,9].

Several recent studies have shown that some growth factors, cytokines and chemokines participate in prostate cancer tumor development[24-29]. Nevertheless, the role of MCP-1 in the regulation of prostate cancer has never been investigated or suggested.

While reducing the present invention to practice, the present inventor uncovered elevated levels of MCP-1 and autoantibodies thereagainst in prostate cancer patients and showed that antibodies which are directed at MCP-1 or a receptor thereof can prevent prostate cancer onset and metastasis. Thus, compositions and methods containing such agents can be utilized for diagnosing and treating prostate cancer.

SUMMARY OF THE INVENTION

According to one aspect of the present invention there is provided a method of treating prostate cancer, the method comprising administering to a subject in need thereof a therapeutically effective amount of an agent capable of reducing activity and/or expression of MCP-1 or of an effector thereof, thereby treating the prostate cancer in the subject.

According to another aspect of the present invention there is provided use of anti-MCP-1 antibody for the manufacture of a medicament for the treatment of prostate cancer.

According to yet another aspect of the present invention there is provided an article-of-manufacture comprising packaging material and a pharmaceutical composition identified for treating prostate cancer being contained within the packaging material, the pharmaceutical composition including, as an active ingredient, an agent capable of reducing activity and/or expression of MCP-1 or of an effector thereof and a pharmaceutically acceptable carrier.

According to still another aspect of the present invention there is provided a method of diagnosing predisposition to, or presence of, prostate cancer in a subject, the method comprising, detecting anti MCP-1 antibodies in a biological sample obtained from the subject, wherein a level above a pre-determined threshold of the anti MCP-1 antibodies in the biological sample, is indicative of the prostate cancer in the subject.

According to an additional aspect of the present invention there is provided a method of diagnosing predisposition to, or presence of, prostate cancer in a subject, the method comprising, detecting MCP-1 expression and/or activity in a prostate tissue obtained from the subject, wherein a level of the MCP-1 expression and/or activity in the prostate tissue is correlative with progression of the prostate cancer in the subject, thereby diagnosing predisposition to, or presence of the prostate cancer in the subject.

According to further features in preferred embodiments of the invention described below, detecting MCP-1 expression is effected by detecting MCP-1 protein.

According to still further features in the described preferred embodiments the effector is CCR-2.

According to still further features in the described preferred embodiments detecting MCP-1 protein is effected via an assay selected from the group consisting of immunohistochemistry, ELISA, RIA, Western blot analysis, FACS analysis, an immunofluorescence assay, and a light emission immunoassay.

According to still further features in the described preferred embodiments the detecting MCP-1 expression is effected by detecting MCP-1 mRNA.

According to still further features in the described preferred embodiments detecting MCP-1 mRNA is effected via an assay selected from the group consisting of PCR, RT-PCR, chip hybridization, RNase protection, in-situ hybridization, primer extension, Northern blot and dot blot analysis.

According to yet an additional aspect of the present invention there is provided a pharmaceutical composition comprising a therapeutically effective amount of an agent capable of reducing activity and/or expression of MCP-1 and/or of an effector thereof and of an anti-prostate cancer drug and a pharmaceutically acceptable carrier or diluent.

According to still further features in the described preferred embodiments the agent is selected from the group consisting of: (i) an oligonucleotide directed to an endogenous nucleic acid sequence expressing the MCP-1 or the effector thereof; (ii) a chemical inhibitor directed to the MCP-1 or the effector thereof; (iii) a neutralizing antibody directed at MCP-1 or the effector thereof; and (iv) a non-functional derivative of the MCP-1 or the effector thereof.

According to still further features in the described preferred embodiments the anti-prostate cancer drug is selected from the group consisting of an androgen suppressing factor, paclitaxel, estramustine, carboplatin and prostate-specific membrane antigen immunizing agents.

The present invention successfully addresses the shortcomings of the presently known configurations by providing novel compositions and methods containing same for diagnosing and treating prostate cancer Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-b are graphs showing high autoantibody titer to MCP-1 in prostate cancer patients. FIG. 1a—Human sera obtained from 23 prostrate cancer patients, 21 patients with non-malignant prostate hyperplasia and 10 control subjects were monitored for possible appearance of autoantibodies to the following 13 chemokines: SDF-1 (CXCL12), MIF, MIP-1α (CCL3), MIP-1β (CCL4), IL-8 (CXCL8), IP-10 (CXCL10), MIP-3α (CCL20), MIP-3β (CCL-19), Lymphotactin (XCL1), MIG (CXCL9), RANTES (CCL5), MCP-3 (CCL7) and MCP-1 (CCL2). A significant antibody response (p<0.01) was detected in vast majority of prostate cancer patients only to MCP-1. FIG. 1b shows the $Log_2Ab$ titer to MCP-1 in each of the above samples. About 82% of CaP patients ($19/23$) and only about 4.7% ($1/21$) of those with non-malignant prostate hyperplasia displayed a significant (log 2Ab titer >10) antibody response to MCP-1 (p<0.01).

FIGS. 2a-g are photomicrographs showing high MCP-1 expression in different pathological grades of human cancer of the prostate (CaP). FIGS. 2a-c are photomicrographs showing H&E staining of different stages of prostate cancer. FIG. 2a—shows a section of the prostate gland from patients with hyperplasia of the prostatic glands (BPH) PSA=5.2; FIG. 2b shows a section of an adenocarcinoma of the prostate Gleason 6(3+3) (intermediate stage) PSA=7.4; FIG. 2c shows a section of a prostate tumor Gleason 9(4+5) (high grade) PSA=68. FIGS. 2d-f are photomicrographs showing respective immunostaining of the above sections with polyclonal anti-human MCP-1 Abs. Note that in all samples, tumor cells as well as smooth muscle cells of the stroma surrounding glandular areas were intensively stained. Intensity of staining correlated with cancer grade. FIG. 2g shows mRNA expression of MCP-1 and CCR2 in androgen-dependent prostate cancer cell line (LNCaP), and androgen-independent cell lines (PC-3, DU-145), as determined by RT-PCR.

FIG. 3a is a photomicrograph showing binding specificity of the polyclonal anti-human MCP-1 antibodies of the present invention, as determined by western blot analysis. Human MCP-1 was cloned from activated monocytes and polyclonal anti-human MCP-1 Abs were generated in rabbits. The specificity of these antibodies was detected by Western blot analysis in which the ability of these Abs to bind either lymphotactin (XCL1), MIP-1α (CCL3), RANTES (CCL5), MCP-3 (CCL7), MIP-3β (CCL19), MIP-3α (CCL20), IL-8 (CXCL8), MIG (CXCL9), IP-10 (CXCL10), SDF-1 (CXCL12) was determined. Expression of each of the factors is shown in the upper panel, binding specificity is demonstrated in the lower panel.

FIGS. 3b-d demonstrate the ability of MCP-1 to induce chemotactic migration and morphological changes of human CaP cell lines, via a G-coupled receptor. FIG. 3b is a photomicrograph showing the migration of LNCaP and PC-3 cell lines towards MCP-1 in a Boyden chamber system. Cells were incubated on top of an 8 μm pore membrane. Lower chambers contained either medium only (control) or medium supplemented with MCP-1 or MCP-1 with the neutralizing anti-MCP-1 Abs, as described above. Chemotaxis index was calculated by dividing cell counts from each membrane by the number of cells from the control membrane. Results are shown as mean percentage triplicates. FIG. 3c is a photomicrograph series (panels a-b) showing membraned of GFP transfected LNCaP (LNCaP.GFP) cells photographed using a fluorescence microscopy after Boyden chamber assays with the lower chamber containing MCP-1 neutralized by Abs (panel a) or MCP-1 alone (panel b). FIG. 3d is a photomicrograph series (panels a-i) illustrating the morphological changes in PC-3 cells treated with recombinant MCP-1. PC-3 cells attached to a plastic dish were exposed to an excessive concentration of recombinant MCP-1 under different conditions, and photographed in 1-minute intervals for a total of 1 hour under light microscopy. Photomicrographs are shown for different time points (0, 30 or 60 minutes following exposure to MCP-1). Control cells without MCP-1 showed no motility (data not shown), while almost all PC-3 cells exposed to the chemokine showed distinct plasma membrane protrusions apparently by actin filament polymerization (panels a-c, arrows). Such prominent cytoskeletal changes occurred instantly following the addition of MCP-1 to the medium, and finally led to cell movement by pseudopodia formation. Medium containing anti-MCP-1 Abs in addition to recombinant MCP-1 (panels d-f) or pretreatment of cells with Wortmannin—a PI-3 kinase inhibitor (panels g-i), produced no significant changes in cell morphology.

FIGS. 4a-b illustrate an autocrine survival activity of MCP-1 on human CaP cell lines. FIG. 4a is a graph showing an anti-proliferative effect of anti-MCP-1 on prostate cancer cells as determined by [$^3$H]-Thymidine incorporation assay. Results are shown as mean CPM of six replicates from 3 independent experiments, divided by the mean CPM of control cells. Proliferation rates of cells cultured with anti-MCP-1 Abs were significantly lower than each of the control groups ($p<0.001$). FIG. 4b is a photomicrograph showing elevation in caspase-3 in prostate cancer cells treated with anti-MCP-1 antibodies, as determined by western blot analysis.

(FIG. 5b) Total weight of mice was also recorded (FIG. 5a). Results are shown as mean 6 mice ±SD. Control mice showed failure to thrive by day 65 and survived 76±5.2 days. In contrast, those treated with anti MCP-1 antibodies did not show any signs of physical distress.

FIGS. 6a-e illustrate the ability of anti-MCP-1 neutralizing antibodies to restrain tumor progression in vivo as determined in a PC-3/SCID mouse model. Mice were injected with PC-3 cells ($5 \times 10^6$ cells/mouse) and treated with anti-MCP-1 antibodies or control IgG, as described in FIGS. 5a-b. Volume of tumor was calculated as $\pi/6ab^2$, where a is the longest dimension, and b is the width. Total weight of mice was also recorded. FIG. 6a presents the tumor volume as a mean of tumors in 6 mice±SD. Control mice showed failure to thrive by day 46 and survived 58±4 days. In contrast, 33% (2/6) of those treated with anti MCP-1 antibodies did not show any signs of physical distress, and the other four survived for more then 80 days. FIG. 6b is a photomicrograph series illustrating the effect of anti-MCP-1 on prostate cancer metastasis, as determined in mice (3 mice per group) which were sacrificed 60 days after the beginning of the experiment. The experiment was condiected by comparing subcutaneous primary tumor of a representative control mouse (panel a), and area of cancer cells inoculation of a treated mouse (panel b). Prior to being sacrificed these mice were subjected to X-Ray image analysis. Control mouse (panel c) revealed large subcutaneous metastasis adjacent to the neck (left arrow) in addition to the primary tumors (right arrow), but no trace of tumor cells was observed in the treated mouse (panel d). FIG. 6c is a photomicrograph series illustrating expression of MCP-1 (panel a) and CCR2 receptor (panel b) on the tumor cells, as determined by immunohistochemistry. FIG. 6d is a photomicrograph series illustrating presence of Tumor associated macrophages (TAM's) close to the tumor margins in an untreated control mouse (panel a), and the absence thereof in a treated mouse (panel b), as determined by immuno-staining with an anti-CD11b mAb. FIG. 6e is a photomicrograph series illustrating the effect of anti-MCP-1 antibodies on blood vessel development in the tumors. Sections from the above tissue samples which were subjected to immuno-staining Control mice (panels a, b) displayed a significantly higher ($p<0.01$, d) number of blood vessels in tumors compared to those previously treated with anti MCP-1 Abs (panel c). Analysis of blood vessels (mean of three counts, at ×400 magnification) is also presented (panel d) ($p<0.01$).

DESCRIPTION OF THE PREFERRED EMBODIMENTS

Figure 5A:
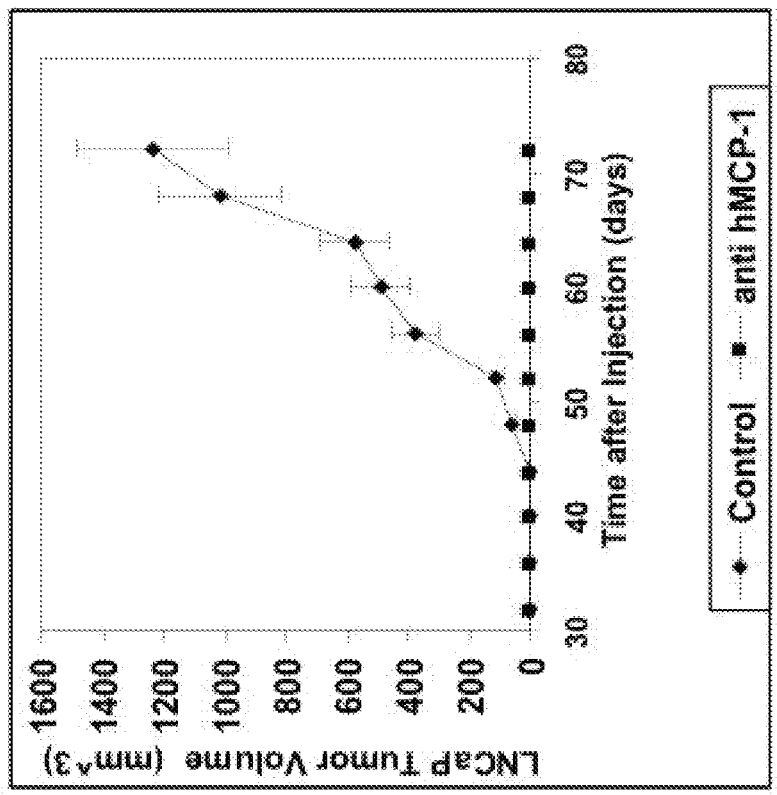
FIGS. 5a-b are graphs illustrating the ability of anti-MCP-1 neutralizing antibodies to prevent tumor progression in vivo as determined in LNCaP/SCID mouse model. A Group of 6 weeks old SCID/Bj mice was subcutaneously injected with LNCaP cells ($8 \times 10^6$ cells/mouse). Four days later mice were randomly separated to two subgroups of 6 mice each that were repeatedly (in a four day interval) administered with either the rabbit anti human MCP-1 antibodies (150 µg/mouse i.v.), or with control IgG from pre-immunized rabbits. An observer blind to the experimental protocol followed the development and progression of the primary tumor. Volume of tumor was calculated as $\pi/6ab^2$, where a is the longest dimension, and b is the width.

The present invention is of compositions which can be used to diagnose and treat prostate cancer. Specifically, the present invention utilizes MCP-1 inhibitors for treating prostate cancer and approaches for detecting MCP-1 activity or expression as in methods of diagnosing prostate cancer.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Prostate cancer has evolved as a major health problem in the male population of the Western world. It is the most commonly diagnosed malignancy and the second leading cause of cancer death, representing nearly 29% of all male cancer deaths. In the year 2001, about 200,000 new cases of prostatic adenocarcinomas were projected in the United States. Prostate cancer is usually an indolent disease, though 25-30% of the tumors become metastatic, resulting in almost 40,000 deaths annually [Parker (1996) CA Cancer J. Clin. 46:5-27]. For these reasons, early detection and efficient treatment of prostate cancer are highly desirable.

MCP-1 is the prototype of the CC family of chemokines. It can recruit monocytes, NK cells, and subpopulations of T lymphocytes, which all express high-affinity receptors, predominantly CCR2. The cytokine plays a major role in autoimmune disease pathogenesis, mostly due to its active function in tissue infiltration of monocytes and T lymphocytes. The role of MCP-1 in tumor development and progression is less clear. Expression of MCP-1 has been reported in melanoma [Graves (1991) Biochem. Pharmacol. 41:333], glioma [Desbaillets (1994) Int. J. Cancer 58:240; Leung (1999) Acta Neutopathol. 93:518], sarcoma [Bottazi (1990) Int. J. Cancer 45:795; Jiang (1990) J. Biol. Chem. 265:18318], leukemia [Selvan (1994) J. Biol. Chem. 269:13893], hemangioma [Isik (1996) J. Surg. Res. 61:71] and carcinomas of the breast [Valkovic (1998) Pathol. Res. Pract. 194:335], cervix [Davidson (1997) Pathol. Res. Pract. 193:491], and ovary [Negus (1995) J. Clin. Invest. 95:2391]. Apparently, MCP-1 can be protective is some tumors, but destructive in others. For example, murine colon carcinoma cells expressing MCP-1 fail to metastesize when injected into mice, whereas other carcinoma cells show enhanced metastasis [Nesbit (2001) The JI 166:6483]. To date, MCP-1 has never been associated with prostate cancer. Rather, gene expression analysis showed reduced expression of MCP-1 in prostate cancer [Chetcuti (2001) Prostate 47(2):132-40], negating an active role of this cytokine in the progression of this disease.

While reducing the present invention to practice, the present inventor uncovered elevated levels of MCP-1, autoantibodies thereagainst, and receptor thereto (CCR2) in prostate cancer patients and showed that anti-MCP-1 can prevent prostate cancer onset and metastasis. Thus, compositions and methods containing this agent can be efficiently utilized for diagnosing and treating prostate cancer.

Thus, according to one aspect of the present invention there is provided a method of treating prostate cancer in a subject in need thereof.

As used herein the term "treating" refers to preventing, curing, reversing, attenuating, alleviating, minimizing, suppressing or halting the deleterious effects of prostate cancer.

As used herein the phrase "prostate cancer" refers to cancers which arise from the glandular tissue (i.e., adenocarcinomas) and to cancers which arise from tissues surrounding the gland (i.e., leiomyosarcoma and rhabdomyosarcoma). Also included in this phrase is prostatic intraepithelial neoplasia which is a benign tumor which eventually becomes malignant. The prostate cancer, according to this aspect of the present invention, can be encapsulated or metastatic.

As used herein the phrase "a subject in need thereof" refers to a mammal, preferably a human subject, who has prostate cancer or is at the risk of developing prostate cancer (i.e., predisposed).

The method, according to this aspect of the present invention, is effected by administering to the subject a therapeutically effective amount of an agent capable of reducing activity and/or expression of MCP-1 or of an effector thereof, to thereby treat the prostate cancer in the subject.

As used herein an MCP-1 refers to an MCP-1 gene product (i.e., protein or mRNA) such as set forth in GenBank Accession Nos. NM_002982 or NP_002973.

An MCP-1 activity refers to signaling (e.g., G protein signaling, JAK/STAT signaling cell-survival, chemotaxis, cell adhesion, angiogensis and prostate cancer progression.

An effector of MCP-1 refers to a molecule, chemical or structure that up-regulates an MCP-1 activity. Thus, an MCP-1 effector can be, for example, the predominant MCP-1 receptor (see Example 7 of the Examples section which follows) i.e., CCR2, CCR2 dimerization, CCR2 tyrosine phosphorylation, down stream signaling components (e.g., Lyn, MAPK) focal adhesion signaling components (e.g., PI3-K and paxillin), assembly thereof, and the JAK/STAT signaling pathway, preferably JAK2/STAT3 [Mellado (1998) J. Immunol. 161:805; Wain (2002) Clin. Exp. Immunol. 127:436; Biswas (2002) Int. Immunopharmacol. 2:1095-107]. Preferably, the effector according to this aspect of the present invention is a specific effector of MCP-1 such as CCR2 (see Example 7 of the Examples section which follows).

A number of agents can be used in accordance with this aspect of the present invention to reduce the activity or expression of MCP-1 or an effector thereof.

Thus, for example the agent can be a neutralizing antibody which inhibits the activity of MCP-1 (such as by binding to the CCR2 binding site on MCP-1) or an effector thereof. An MCP-1 neutralizing antibody is described in the materials and experimental procedure section of the Examples section which follows). Other neutralizing antibodies for MCP-1 are known in the art. See for example Yamada et al. Arterioscler. Thromb. Vasc. Biol. (2003) 23:1996-2001.

The term "antibody" refers to whole antibody molecules as well as functional fragments thereof, such as Fab, $F(ab')_2$, and Fv that are capable of binding with antigenic portions of the target polypeptide. These functional antibody fragments constitute preferred embodiments of the present invention, and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule as described in, for example, U.S. Pat. No. 4,946,778.

Purification of serum immunoglobulin antibodies (polyclonal antisera) or reactive portions thereof can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (see Goding in, Monoclonal Antibodies: Principles and Practice, 2nd ed., pp.

104-126, 1986, Orlando, Fla., Academic Press). Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains. Additional classes include IgD, IgE, IgA, IgM and related proteins.

Methods of generating and isolating monoclonal antibodies are well known in the art, as summarized for example in reviews such as Tramontano and Schloeder, Methods in Enzymology 178, 551-568, 1989. A recombinant MCP-1 polypeptide may be used to generate antibodies in vitro (see the materials and experimental procedures section of the Examples section which follows). More preferably, the recombinant protein is used to elicit antibodies in vivo. In general, a suitable host animal is immunized with the recombinant MCP-1. Advantageously, the animal host used is a mouse of an inbred strain. Animals are typically immunized with a mixture comprising a solution of the recombinant MCP-1 in a physiologically acceptable vehicle, and any suitable adjuvant, which achieves an enhanced immune response to the immunogen. By way of example, the primary immunization conveniently may be accomplished with a mixture of a solution of the recombinant MCP-1 and Freund's complete adjuvant, said mixture being prepared in the form of a water in oil emulsion. Typically the immunization will be administered to the animals intramuscularly, intradermally, subcutaneously, intraperitoneally, into the footpads, or by any appropriate route of administration. The immunization schedule of the immunogen may be adapted as required, but customarily involves several subsequent or secondary immunizations using a milder adjuvant such as Freund's incomplete adjuvant. Antibody titers and specificity of binding to the MCP-1 can be determined during the immunization schedule by any convenient method including by way of example radioimmunoassay, or enzyme linked immunosorbant assay, which is known as the ELISA assay. When suitable antibody titers are achieved, antibody-producing lymphocytes from the immunized animals are obtained, and these are cultured, selected and cloned, as is known in the art. Typically, lymphocytes may be obtained in large numbers from the spleens of immunized animals, but they may also be retrieved from the circulation, the lymph nodes or other lymphoid organs. Lymphocytes are then fused with any suitable myeloma cell line, to yield hybridomas, as is well known in the art. Alternatively, lymphocytes may also be stimulated to grow in culture, and may be immortalized by methods known in the art including the exposure of these lymphocytes to a virus, a chemical or a nucleic acid such as an oncogene, according to established protocols. After fusion, the hybridomas are cultured under suitable culture conditions, for example in multi-well plates, and the culture supernatants are screened to identify cultures containing antibodies that recognize the hapten of choice. Hybridomas that secrete antibodies that recognize the recombinant MCP-1 are cloned by limiting dilution and expanded, under appropriate culture conditions. Monoclonal antibodies are purified and characterized in terms of immunoglobulin type and binding affinity.

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, in U.S. Pat. Nos. 4,036,945 and 4,331,647, and references contained therein, which patents are hereby incorporated by reference in their entirety (see also Porter, R. R., Biochem. J., 73: 119-126, 1959). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al. (Proc. Nat'l Acad. Sci. USA 69:2659-62, 1972). Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, all of which are hereby incorporated, by reference, in entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick and Fry Methods, 2: 106-10, 1991).

Humanized forms of non-human (e.g., murine) antibodies are chimeric molecules of immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues, which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source, which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human monoclonal antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

An agent for reducing the activity of MCP-1 or an effector thereof can also be a non-functional derivative thereof (i.e., dominant negative). For example, artificial dominant negative molecules of MCP-1 have been previously described by Egashira (2003) Hypertension 41:834-41 and by Zhang (1995) Mol. Cell. Biol. 15:4851-4855. This molecule includes an N-terminal deletion (i.e., amino acids 2-8) and acts as a dominant negative inhibitor of MCP-1. Alternatively, as mentioned, the dominant negative molecule can be directed at an MCP-1 effector molecule, such as for example Rho [i.e., RhoT19N Stamatovic (2003) J. Cell Sci. 116:4615-28] and dominant negative Stat3 [e.g., truncated Stat3 and Stat3 Y705F, as described by Oh (2000) Blood 96:65 and Kaptein (1996) J. Biol. Chem. 271:5961-5964].

It will be appreciated that when available, naturally occurring non-functional derivatives of the pathway can be used. Thus, for example, the present invention can use the natural inhibitor of Stat 3, PIAS3 previously described by Chung (1997) Science 278:1803.

Polypeptides of these non-functional derivatives can be synthesized using solid phase peptide synthesis procedures which are well known in the art and further described by John Morrow Stewart and Janis Dillaha Young, Solid Phase Peptide Syntheses (2nd Ed., Pierce Chemical Company, 1984). Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the proteins are desired, they can be generated using recombinant techniques such as described by Bitter et al., (1987) Methods in Enzymol. 153: 516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

Alternatively, these proteins can encoded expressed within the target cell from an exogenous polynucleotides ligated into a nucleic acid expression construct.

It will be appreciated that the nucleic acid construct can be administered to the individual employing any suitable mode of administration, described hereinbelow (i.e., in-vivo gene therapy). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

To enable cellular expression of the polynucleotides of the present invention, the nucleic acid construct of the present invention further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any suitable promoter sequence can be used by the nucleic acid construct of the present invention.

Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (for details see Invitrogen website). Examples of retroviral vector and packaging systems are those sold by Clontech, San Diego, Calif., including Retro-X vectors pLNCX and pLXSN, which permit cloning into multiple cloning sites and the trasgene is transcribed from CMV promoter. Vectors derived from Mo-MuLV are also included such as pBabe, where the transgene will be transcribed from the 5'LTR promoter.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Alternatively, the agent of this aspect of the present invention can be a chemical, which is designed to specifically inhibit the activity or expression of MCP-1 or an effector thereof. For example, thiazolidinedione can be used to inhibit MCP-1 expression [Momoi (2001) Chest 120:1293-300], other MCP-1 inhibitors are described is U.S. Pat. Nos. 6,441,004, 6,291,507, EP-01056451 and by Amann (2003) Diabetes Care 26:2421. Chemical inhibitors directed at MCP-1 effectors are well known in the art. Examples include, but are not limited to, Y27632, a Rho kinase inhibitor and wortmanin, a PI3K inhibitor, Cytovaricin B, a Jak/Stat inhibitor [Seto (1997) J. of Antibiotics 50:440], AG-490, a Jak inhibitor and CCR2 receptor antogonists (Incyte Corp. and U.S. Pat. No. 6,613,760). Signal transduction inhibitors are available from a number of chemical companies including Calbiochem (San Diego, Calif., USA) and Sigma-Aldrich Corp. (St Louis, Mo., USA). Additional Jak/Stat inhibitors are described in U.S. Pat. Nos. 6,265,160, 6,210,654 and 6,187,552.

Another agent capable of reducing the expression of MCP-1 or effectors thereof is a small interfering RNA (siRNA) molecule. RNA interference is a two-step process. the first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA), each with 2-nucleotide 3' overhangs [Hutvagner and Zamore Curr. Opin. Genetics and Development 12:225-232 (2002); and Bernstein Nature 409:363-366 (2001)].

In the effector step, the siRNA duplexes bind to a nuclease complex to from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al. (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, an MCP-1 mRNA sequence, for example, is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (for details see the Ambion Inc. web site, item "techlib/tn/91/912").

Second, potential target sites are compared to an appropriate genomic database (e.g., human, mouse, rat etc.) using any sequence alignment software, such as the BLAST software available from the NCBI server (see "BLAST" at the NCBI.gov website). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation.

For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

Another agent capable of downregulating MCP-1 or an effector thereof is a DNAzyme molecule capable of specifically cleaving an mRNA transcript or DNA sequence of interest. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine: pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 2002, Abstract 409, Ann Meeting Am Soc Gen Ther, available at the American Society for Gene Therapy website). In another application, DNAzymes complementary to bcr-ab1 oncogenes were successful in inhibiting the oncogenes expression in leukemia cells, and lessening relapse rates in autologous bone marrow transplant in cases of CML and ALL.

Reducing MCP-1 or an effector thereof can also be effected by using an antisense polynucleotide capable of specifically hybridizing with an mRNA transcript encoding the proteins of interest.

Design of antisense molecules which can be used to efficiently downregulate a a gene product of interest must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

MCP-1 antisense molecules have been previously described by Ghirnikar (1998) Neuroscience letters 247:21-24 and Tolnosugi (1996) J. Am. Soc. Nephrology 7:1748.

Another agent capable of reducing the expression of MCP-1 or an effector thereof is a ribozyme molecule capable of specifically cleaving an mRNA transcript encoding this gene product. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

An additional method of reducing the expression of an MCP-1 gene or effectors thereof in cells is via triplex forming oligonucleotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245: 725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| oligo | 3'--A | G | G | T |
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, September 12, Epub). The same authors have demonstrated that TFOs designed according to the A-AT and G-GC rule do not form non-specific triplexes, indicating that the triplex formation is indeed sequence specific.

Thus for any given sequence a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

Additional description of oligonucleotide agents is further provided hereinbelow. It will be appreciated that therapeutic oligonucleotides may further include base and/or backbone modifications which may increase bioavailability therapeutic efficacy and reduce cytotoxicity. Such modifications are described in Younes (2002) Current Pharmaceutical Design 8:1451-1466.

For example, the oligonucleotides of the present invention may comprise heterocylic nucleosides consisting of purines and the pyrimidines bases, bonded in a 3' to 5' phosphodiester linkage.

Preferably used oligonucleotides are those modified in either backbone, internucleoside linkages or bases, as is broadly described hereinunder.

Specific examples of preferred oligonucleotides useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides which can be used according to the present invention, are those modified in both sugar and the internucleoside linkage, i.e., the backbone, of the nucleotide units are replaced with novel groups. The base units are maintained for complementation with the appropriate polynucleotide target. An example for such an oligonucleotide mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No. 6,303,374.

Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

It will be appreciated that the agent according to this aspect of the present invention can be also a molecule, which promotes specific immunogenic response to MCP-1 or an effector thereof in the subject. Thus, for example, the molecule can be an MCP-1 protein, a fragment derived therefrom or a nucleic acid sequence encoding same. Such a molecule is set forth in SEQ ID NO: 12 or the nucleic acid coding sequence set forth in SEQ ID NO: 11 (primers thereto are provided in SEQ ID NOs: 13 and 6). Although such a molecule can be provided to the subject per se, the agent is preferably administered with an immunostimulant in an immunogenic composition.

An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes into which the compound is incorporated (see e.g., U.S. Pat. No. 4,235,877).

Vaccine preparation is generally described in, for example, M. F. Powell and M. J. Newman, eds., "Vaccine Design (the subunit and adjuvant approach)," Plenum Press (NY, 1995).

Illustrative immunogenic compositions may contain DNA encoding MCP-1, such that the protein is generated in situ. The DNA may be present within any of a variety of delivery systems known to those of ordinary skill in the art, including nucleic acid expression systems, bacteria and viral expression systems. Gene delivery techniques are well known in the art, such as those described by Rolland, Crit. Rev. Therap. Drug Carrier Systems 15:143-198, 1998, and references cited therein.

Preferably, the DNA is introduced using a viral expression system (e.g., vaccinia or other pox virus, retrovirus, lentivirus or adenovirus), which may involve the use of a non-pathogenic (defective), replication competent virus. Suitable systems are disclosed, for example, in Fisher-Hoch et al., Proc. Natl. Acad. Sci. USA 86:317-321, 1989; Flexner et al., Ann. N.Y. Acad. Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993.

Techniques for incorporating DNA into such expression systems are well known to those of ordinary skill in the art. The DNA may also be "naked," as described, for example, in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

It will be appreciated that an immunogenic composition may comprise both a polynucleotide and a polypeptide component. Such immunogenic compositions may provide for an enhanced immune response.

Any of a variety of immunostimulants may be employed in the immunogenic compositions of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

The adjuvant composition may be designed to induce an immune response predominantly of the Th1 type. High levels of Th1-type cytokines (e.g., IFN-.gamma., TNF.alpha., IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of an immunogenic composition as provided herein, the subject will support an immune response that includes Th1- and Th2-type responses. The levels of these cytokines may be readily assessed using standard assays. For a review of the families of cytokines, see Mosmann and Coffman, Ann. Rev. Immunol. 7:145-173, 1989.

Preferred adjuvants for use in eliciting a predominantly Th1-type response include, for example, a combination of monophosphoryl lipid A, preferably 3-de-β-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., Science 273:352, 1996. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720.

A delivery vehicle can be employed with the immunogenic composition of the present invention in order to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Dendritic cells are highly potent APCs (Banchereau and Steinman, Nature 392:245-251, 1998) and have been shown to be effective as a physiological adjuvant for eliciting prophylactic or therapeutic antitumor immunity (see Timmernan and Levy, Ann. Rev. Med. 50:507-529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within an immunogenic composition (see Zitvogel et al., Nature Med. 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNF.alpha. to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNF.alpha., CD40 ligand, LPS, flt3 ligand and/or other compound(s) that induce differentiation, maturation and proliferation of dendritic cells.

Dendritic cells are categorized as "immature" and "mature" cells, which allows a simple way to discriminate between two well characterized phenotypes. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding MCP-1, such that MCP-1, or an immunogenic portion thereof, is expressed on the cell surface. Such transfection may take place ex vivo, and a composition comprising such transfected cells may then be used for therapeutic purposes, as described herein. Alternatively, a gene delivery vehicle that targets a dendritic or other antigen presenting cell may be administered to the subject, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and cell Biology 75:456-460, 1997. Antigen loading of dendritic cells may be achieved by incubating dendritic cells or progenitor cells with the MCP-1 polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule) such as described above. Alternatively, a dendritic cell may be pulsed with a non-conjugated immunological partner, separately or in the presence of the polypeptide.

It will be appreciated that selection of agents which are capable of reducing the activity or expression of MCP-1 or effectors thereof is preferably effected by examining their effect on at least one of the above-described MCP-1 activities. This can be effected using a number of biochemical (e.g., western blot analysis), cell-biology (e.g., cell migration and immunostaining) and molecular biology (e.g., RT-PCR) methods which are well known in the art and are described in details in the materials and experimental procedures section of the Examples section which follows.

The above-described agents for reducing expression or activity of MCP-1 or of effectors thereof (i.e., active ingredients) can be provided to the subject per se, or as part of a pharmaceutical composition where they are mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the preparation accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Pharmaceutical compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It will be appreciated that treatment of prostate cancer according to the present invention may be combined with other treatment methods known in the art (i.e., combination therapy), such as, radical or salvage prostatectomy, external beam irradiation therapy, interstitial seed implantation (brachytherapy), hormonal therapy and androgen ablation and chemotherapy (for additional information on treatment options available to date see the website "psa-rising.com", under "medical txmodes").

In general, the contribution of MCP-1 in either supporting tumor growth or suppressing it is controversial. Transfection of tumor cells with MCP-1 can prevent tumor formation and decrease metastasis [[Rollins (1991) Mol. Cell. Biol. 11:3125; while in other tumors a destructive role has been attributed to MCP-1, for example increasing tumorigenicity and lung metastasis [Bottazzi (1992) J. Immunol. 148:1280].

Thus, the present invention also envisages treatment of cancers, other than prostate cancer, for which no association with MCP-1 or a protective role for MCP-1 has been found to date, using the above-described methodology.

In addition to therapeutic advances pioneered by the present invention, the unprecedented findings that MCP-1, antibodies thereagainst and a receptor thereto (i.e., CCR2) are expressed in prostate cancer cells in direct correlation with cancer progression may be also employed in diagnostic applications (see Examples 1-2 of the Examples section which follows).

Thus, according to another aspect of the present invention there is provided a method of diagnosing predisposition to, or presence of, prostate cancer in a subject.

As used herein the term "diagnosing" refers to classifying a disease or a symptom as a prostate cancer, determining a severity of a prostate cancer, monitoring disease progression, forecasting an outcome of a disease and/or prospects of recovery.

The method is effected by detecting MCP-1, antibodies thereagainst and/or receptors thereto (e.g., CCR2) in a biological sample obtained from the subject, wherein each of the levels determined can be correlated with progression of the prostate cancer in the subject, to thereby diagnose predisposition to, or presence of the prostate cancer in the subject As used herein, the term "level" refers to expression levels of RNA and/or protein or to DNA copy number of MCP-1, antibodies thereagainst and/or receptors thereto.

A level correlatable with predisposition to, or presence or absence of prostate cancer can be a level of MCP-1, antibodies thereagainst and/or receptors thereto in a prostate cancer sample which is increased as compared to the level of the same in a normal healthy sample obtained from a similar tissue or cellular origin.

As used herein "a biological sample" refers to a sample of tissue or fluid isolated from a subject, including but not limited to, for example, plasma, serum, spinal fluid, lymph fluid, the external sections of the skin, respiratory, intestinal, and genitourinary tracts, tears, saliva, milk, blood cells, tumors, organs, and also samples of in vivo cell culture constituents.

Numerous well known tissue or fluid collection methods can be utilized to collect the biological sample from the subject in order to determine the level of each of the above-described proteins in the subject. Examples include, but are not limited to, fine needle biopsy, needle biopsy, core needle biopsy and surgical biopsy. Preferably, biopsying of the primary tumor is effected by prostate needle biopsy.

Regardless of the procedure employed, once a biopsy is obtained the level of MCP-1, antibodies thereagainst and/or receptors thereto can be determined and a diagnosis can thus be made.

Determining a level of MCP-1, antibodies thereagainst and/or receptors thereto can be effected using various biochemical and molecular approaches used in the art for determining gene amplification, and/or level of gene expression.

Typically, detection of a nucleic acid of interest in a biological sample is effected by hybridization-based assays using an oligonucleotide probe.

The term "oligonucleotide" refers to a single stranded or double stranded oligomer or polymer of ribonucleic acid (RNA) or deoxyribonucleic acid (DNA) or mimetics thereof. This term includes oligonucleotides composed of naturally-occurring bases, sugars and covalent internucleoside linkages (e.g., backbone) as well as oligonucleotides having non-naturally-occurring portions which function similarly to respective naturally-occurring portions. An example of an oligonucleotide probe which can be utilized by the present invention to specifically detect the presence of MCP-1 mRNA is as set forth in SEQ ID NO: 9 or 10.

Oligonucleotides designed according to the teachings of the present invention can be generated according to any oligonucleotide synthesis method known in the art, such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

The oligonucleotide of the present invention is of at least 17, at least 18, at least 19, at least 20, at least 22, at least 25, at least 30 or at least 40, bases specifically hybridizable with the examined mRNA.

Hybridization based assays which allow the detection of a DNA or RNA of interest in a biological sample rely on the use of oligonucleotide which can be 10, 15, 20, or 30 to 100 nucleotides long preferably from 10 to 50, more preferably from 40 to 50 nucleotides.

Hybridization of short nucleic acids (below 200 bp in length, e.g. 17-40 bp in length) can be effected using the following examplery hybridization protocols which can be modified according to the desired stringency; (i) hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 1-1.5° C. below the $T_m$, final wash solution of 3 M TMACl, 0.01 M sodium phosphate (pH 6.8), 1 mM EDTA (pH 7.6), 0.5% SDS at 1-1.5° C. below the $T_m$; (ii) hybridization solution of 6×SSC and 0.1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 2-2.5° C. below the $T_m$, final wash solution of 3 M TMACl, 0.01 M sodium phosphate (pH 6.8), 1 mM EDTA (pH 7.6), 0.5% SDS at 1-1.5° C. below the $T_m$, final wash solution of 6×SSC, and final wash at 22° C.; (iii) hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature.

The detection of hybrid duplexes can be carried out by a number of methods. Typically, hybridization duplexes are separated from unhybridized nucleic acids and the labels bound to the duplexes are then detected. Such labels refer to radioactive, fluorescent, biological or enzymatic tags or labels of standard use in the art. A label can be conjugated to either the oligonucleotide probes or the nucleic acids derived from the biological sample (target).

For example, oligonucleotides of the present invention can be labeled subsequent to synthesis, by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, when fluorescently-labeled oligonucleotide probes are used, fluorescein, lissamine, phycoerythrin, rhodamine (Perkin Elmer Cetus), Cy2, Cy3, Cy3.5, Cy5, Cy5.5, Cy7, Fluor X (Amersham) and others [e.g., Kricka et al. (1992), Academic Press San Diego, Calif] can be attached to the oligonucleotides.

Traditional hybridization assays include PCR, RT-PCR, RNase protection, in-situ hybridization, primer extension, Southern blot, Northern Blot and dot blot analysis.

Those skilled in the art will appreciate that wash steps may be employed to wash away excess target DNA or probe as well as unbound conjugate. Further, standard heterogeneous assay formats are suitable for detecting the hybrids using the labels present on the oligonucleotide primers and probes.

It will be appreciated that a variety of controls may be usefully employed to improve accuracy of hybridization assays. For instance, samples may be hybridized to an irrelevant probe and treated with RNAse A prior to hybridization, to assess false hybridization.

Polymerase chain reaction (PCR)-based methods may be used to identify the presence of mRNA of interest. For PCR-based methods a pair of oligonucleotides is used, which is specifically hybridizable with the polynucleotide sequences described hereinabove in an opposite orientation so as to direct exponential amplification of a portion thereof (including the hereinabove described sequence alteration) in a nucleic acid amplification reaction.

The polymerase chain reaction and other nucleic acid amplification reactions are well known in the art and require no further description herein. The pair of oligonucleotides according to this aspect of the present invention are preferably selected to have compatible melting temperatures (Tm), e.g., melting temperatures which differ by less than that 7° C., preferably less than 5° C., more preferably less than 4° C., most preferably less than 3° C., ideally between 3° C. and 0° C.

Hybridization to oligonucleotide arrays may be also used to determine the presence of the mRNA or DNA of interest. Such screening has been undertaken in the BRCA1 gene and in the protease gene of HIV-1 virus [see Hacia et al., (1996) Nat Genet 1996; 14(4):441-447; Shoemaker et al., (1996) Nat Genet 1996; 14(4):450-456; Kozal et al., (1996) Nat Med 1996; 2(7):753-759].

The nucleic acid sample which includes the candidate region to be analyzed is isolated, amplified and labeled with a reporter group. This reporter group can be a fluorescent group such as phycoerythrin. The labeled nucleic acid is then incubated with the probes immobilized on the chip using a fluidics station. For example, Manz et al. (1993) Adv in Chromatogr 1993; 33:1-66 describe the fabrication of fluidics devices and particularly microcapillary devices, in silicon and glass substrates.

Once the reaction is completed, the chip is inserted into a scanner and patterns of hybridization are detected. The hybridization data is collected, as a signal emitted from the reporter groups already incorporated into the nucleic acid, which is now bound to the probes attached to the chip. Since the sequence and position of each probe immobilized on the chip is known, the identity of the nucleic acid hybridized to a given probe can be determined.

It will be appreciated that when utilized along with automated equipment, the above described detection methods can be used to screen multiple samples for prostate cancer both rapidly and easily.

The level of MCP-1, antibodies thereagainst and/or receptors thereto may also be determined at the protein level. Numerous protein detection assays are known in the art, examples include, but are not limited to, chromatography, electrophoresis, immunodetection assays such as ELISA and western blot analysis, immunohistochemistry and the like, which may be effected using antibodies such as described hereinabove. Note, however, that such antibodies need not be neutralizing antibodies.

Diagnosis of prostate cancer using the above-described methodology can be further supported by other diagnostic methods for prostate cancer which are well known in the art to thereby provide a more accurate diagnosis. Examples of such diagnostic methods include, but are not limited to, the prostate specific antigen (PSA) test, which measures the level of free and bound PSA in the blood; the prostatic acid phosphatase (PAP) blood test; trans rectal ultrasound (TRUS); CT-scan; bone scan; MRI; surgical biopsy; the TNM (tumor, node, metastasis) cancer staging system, wherein cancer is staged according to: T=the type of tumor N=tumor spread to the lymph nodes M=tumor spread to distant sites, and the Gleason grade which is further described in Example 2 of the Examples section which follows.

It will be appreciated that the diagnostic reagents described hereinabove can also be included in kits. For example a kit for diagnosing predisposition to, or presence of prostate cancer in a subject can include the antibody described in the Examples section in a one container and a solid phase for attaching multiple biological samples packaged in a second container with appropriate buffers and preservatives and used for diagnosis.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Procedures

Patients and Tumor Specimens—

Sera from 23 prostate cancer patients, 21 patients with non-malignant prostate hyperplasia (BPH) and 11 control subjects, were monitored for possible appearance of autoantibodies to the following chemokines: SDF-1 (CXCL12, GenBank Accession No. NM_199168), MIF (GenBank Accession No. NM_002415), MIP-1a (CCL3, GenBank Accession No. NM_002983), MIP-1b (CCL4, GenBank Accession No. NM_002984), IL-8 (CXCL8, GenBank Accession No. NM_000584), IP-10 (CXCL10, GenBank Accession NM_001565), MIP-3a (CCL20, GenBank Accession No. NM_004591), MIP-3b (CCL19, GenBank Accession No. NM_006274), Lymphotactin (XCL1, GenBank Accession No. NM_002995), MIG (CXCL9, GenBank Accession No. NM_002416), RANTES (CCL5, GenBank Accession No. NM_002985), MCP-3 (CCL7, GenBank Accession No. NM_006273) and MCP-1 (CCL2, GenBank Accession No. NM_002982) using an ELISA test, as further described hereinbelow.

Tumor specimens dissected from patients were provided by the Urology department of Carmal medical center, to test the tissue for MCP-1 and CCR2 expression, using immunohistochemistry methods, as further described hereinbelow.

Animals—

Male SCID/Beige mice, about 6 weeks old, were purchased from Harlan (Jerusalem, Israel), and kept under special pathogen-free conditions in the Technion's animal facility.

Female NZW rabbits, about 1 kg, were purchased from Harlan (Jerusalem, Israel) and kept under special pathogen-free conditions in the Technion's animal facility.

Cells—

Human LNCaP cells (hormone sensitive, ATCC CAT. NO.—CRL-1740) were originally isolated from a lymph node of a CaP patient with disseminated bony and lymph node involvement. PC-3 cells (hormone insensitive, ATCC CAT. NO. CRL-1435) were isolated from a vertebral metastasis of a human CaP patient, and DU-145 cells (hormone insensitive, ATCC CAT. NO.—HTB-81) were isolated from a lesion in the brain of a patient with metastatic carcinoma of the prostate and a 3 year history of lymphocytic leukemia. All cell lines were obtained from American Type Culture Collection (ATCC, Rockville, Md.). CaP cell lines were passaged and allowed to grow to confluence over 5 days. The cells were cultured in RPMI 1640 supplemented with 10% fetal calf serum (FCS), 1% HEPES 1M, 0.1% Transferin, and 50 µg/ml Gentamycin. PC-3 cells expressing the luciferase gene (PC-3.luc) were obtained from Prof. Yefeanof, Lautenberg center for Immunology, Hadassah Hospital, and LN-CaP cells expressing the Green Fluorescence Protein (GFP) (LN-CaP.GFP) were obtained from Prof. Karl Skortsky, Rappaport faculty of medicine, Technion.

The THP-1 cell line (ATCC CAT. NO.—TIB-202) was cultured in RPMI 1640 medium, supplemented with 5% FCS, 1% penicillin-streptomycin, and 1% L-glutamine. Unless otherwise indicated all culturing reagents were purchased from Beit Ha'emek biological industries.

RT-PCR—

Cell lines were lysed using TRI Reagent (Sigma-Aldrich, St. Louis, Mo.), and total RNA was extracted according to manufacturer's instructions. Reverse transcriptase reaction (RT) was effected on 2 µg of total RNA, using reverse transcriptase (New England Biolabs, Beverly, Mass.) and random primers (Invitrogen, San Diego, Calif.). Oligonucleotide Primers specific for human MCP-1 (5'-ATGAAAGTCTCT-GCCGCCCTTC-3', SEQ ID NO: 1 and 5'-TCAAGTCT-TCGGAGTTTGGGTT-3', SEQ ID NO: 2), or for human CCR2 (5'-ATGCTGTCCACATCTCGTTCTC-3, SEQ ID NO: 3' and 5'-CCAACCAGGTGATCACACTTGT-3', SEQ ID NO: 4) were designed based on published sequences at NCBI (National Center for Biotechnology Information, GenBank Accession Nos. are indicated above). Primers were then used to amplify the cDNA by 25 PCR cycles, with a thermal cycle profile of denaturation for 1 min at 95° C., annealing for 1 min at 55° C., and extension for 1 min at 72° C. Once PCR reactions were terminated, the mixtures were loaded onto a 5% polyacrylamide gel in TAE buffer. MCP-1 PCR product was cloned and sequenced.

Cloning of Human MCP-1— cDNA obtained by the above-described RT reaction was amplified using specific oligonucleotide primers for human MCP-1 without its Signal Peptide sequence, containing cleavage sites for EcoRV—EcoRI [5'(EcoRV)-GCT-GATATCCAGCCAGATGCAATCAATGC-3' SEQ ID NO: 5, and 5'-(EcoRI)-CCGGAATTCTCAAGTCTTCG-GAGTTTGGG-3', SEQ ID NO: 6], then cleaved with restriction enzymes (EcoRV, EcoRI) and cloned to pET-30a (Novagen, EMD Biosciences, Madison, Wis.) and transformed to *Escherichia coli*. Sequence was verified.

Production and Purification of rMCP-1—

The above PCR product (SEQ ID NO: 7) was expressed in *E. coli* (QIAGEN, Chatsworth, Calif., USA) and then purified (SEQ ID NO: 8) by an NI-NTA-supper flow affinity purification of 6×His proteins (Qiagen, Chatsworth, Calif., USA). Purification of rMCP-1 was verified by gel electrophoresis, by Western blotting with specific Anti-Human MCP-1 polyclonal antibodies (PeproTech, Rocky Hill, N.J.) and by sequencing.

Western Blot Analysis for rMCP-1—

The following proteins: SDF-1 (CXCL12), MIF, MIP-1a (CCL3), MIP-1b (CCL4), IL-8 (CXCL8), IP-10 (CXCL10), MIP-3a (CCL20), MIP-3b (CCL-19), Lymphotactin (XCL1), MIG (CXCL9), RANTES (CCL5), MCP-3 (CCL7), MCP-1 (CCL2) (PeproTech), and rMCP-1, produced as described above, were separated by SDS-PAGE electrophoresis, using a 17% bis-acrylamide running gel. The nonstained gel was then transferred to Hybond-ECL nitrocellulose membrane (Amersham Biosciences, Piscataway, N.J.) in a semidry blotting unit (Amersham Pharmacia, San Francisco, Calif.) applying 0.85 mA/cm$^2$ membrane. Nonspecific binding to the membrane was blocked by incubation with 5% skim milk powder in TBS (50 mM Tris-HCl, pH 7.6, 145 mM NaCl) containing 0.1% Tween-20 (TBST) for 2 h under gentle shaking. Following washing the membranes with TBST, a primary Ab (0.2 µg/ml) in TBST buffer containing 5% skim milk was added to the membrane and incubated for 3 h. Subsequently, membranes were washed with TBST and incubated with secondary biotin-SP-conjugated goat anti-rabbit IgG Ab (Jackson ImmunoResearch Laboratories, West Grove, Pa.) for another 1 hour. After washing the membrane with TBST, membranes were incubated with HRP-Streptavidin (Jackson ImmunoResearch Laboratories, West Grove, Pa.), washed once more, and an ECL reaction was conducted using EZ-ECL (Biological Industries, Beit Haemek, Israel) or Luminol Reagent kit (Santa Cruz Bisotechnology, Santa Cruz, Calif.). Membranes were exposed to Super RX X-Ray films (Fujifilm, Tokyo, Japan).

Human CaP Tumor Formation in SCID Mice—

6 weeks old SCID/Bg mice were injected subcutaneously between the two flanks with 300 µl PBS containing LNCaP ($8 \times 10^6$ cells/mouse) or PC-3 ($5 \times 10^6$/mouse) cells which were trypsinized and PBS-double-washed. All SCID mice were monitored daily for evidence of illness. Two days after injection of cancer cells, mice were divided randomly into 3 groups: One group was untreated, another was injected with 150 µg/mouse total (preimmune) rabbit IgG, and a third one received 150 µg/mouse polyclonal rabbit anti human-MCP-1 antibodies every 4 days into the tail vein. Every 4 days, from injection mice were weighed, and tumor diameters were measured using a caliper. Tumor volume was calculated using the formula $\pi/6 \times a \times b^2$, where a is the longest dimension, and b is the width. Mice were then X-Ray filmed, sacrificed, photographed, and tumors or other organs dissected for immunohistochemistry. Tumor volumes were evaluated by soaking the tumors in a PBS column.

Immunohistochemistry—

Human or mouse tumors, or other organ samples for immunohistochemistry were fixed in 10% formalin in PBS over night, dehydrated through graded alcohol and chloroform, and embedded in paraffin. Serial 5-7 µm sections were cut and stained with hematoxylin and eosin.

Immunohistochemistry was effected on serial sections by an immunoperoxidase technique, using streptavidin-peroxidase and AEC substrate chromogen kit (Zymed). Tissue samples were deparaffinized, incubated with 3% $H_2O_2$ for 20 min to avoid endogenous peroxidase activity, and blocked using a non immune blocking solution (Zymed) for 20 min. PBS diluted primary antibodies were incubated for 3 h or over night. After three washes, rabbit or mouse secondary antibody was added for 1 h, followed by PBS rinsing. Following peroxidase staining, slides were counterstained lightly with hematoxylin. The following antibodies were used as primary Abs: anti-human MCP-1 (PeproTech, Rocky Hill, N.J.), anti-human CCR2 (Santa Cruz Bisotechnology, Santa Cruz, Calif.), anti-mouse CD11b (Mac-1α-chain, BD Pharmingen, San Diego, Calif.) to detect mouse macrophages and anti-mouse CD31 [platelet endothelial cell adhesion molecule-1 (PECAM-1, BD Pharmingen, San Diego, Calif.). Vessel counts were determined by light microscopy in tumor areas which contain the highest numbers of capillaries and small venules at the invasive edge. Highly vascular areas were identified by scanning tumor sections at low power. Once the 6 areas of highest neovascularization were identified, vessel counts were effected, and the average count for the 6 fields was determined.

In Vivo and In Vitro Light Detection—

A group of SCID/Bg mice were injected with luciferase expressing PC-3 cells ($8 \times 10^6$ cells/mouse) treated as described above. For detection of light emitted from mice a Roper Chemiluminescence Imaging System, the cooled CCD (CCCD) model LN/CCD-1300EB equipped with ST-133 controller and a 50 mm Nikon lens (Roper Scientific, Princeton Instrument, Trenton, N.J.) was used. Acquisitions were taken 22 and 42 days following injection of cancer cells. Each mouse was anesthetized by injection of 1500 Xylazine (V.M.D., Arendonk, Belgium), in 8500 Ketamine (Fort Dodge Animal Health, Fort Dodge, Lowa), followed by an I.P. injection of 3.15 mg luciferin (Promega Corp., Madison, Wis.) in 500 µl sterile PBS. Exposure time was always 2 min per mouse, 20 min after luciferin administration. Efficiency of photons to electrons conversion is about 90% in the wavelength emission range of luciferase-luciferin for the camera, with a conversion rate of about 1.8 electrons per count. After acquisition, measurement was by defining a Region Of Interest (ROI). Measurements were a total sum integrated signal in a standard period of time subtracted by the background area of equal size. An increase in ROI size had no appreciable effect on the total measured intensity.

For detection of micro-metastases, the luciferase 1000 assay system (Promega) was used, according to the manufacturer's instructions. Spleen, lymph nodes, liver, lungs, testicles, brain and long bones were harvested and homogenized in lysis buffer (Promega). The TD-20/20 Luminometer (Turner Designs, Inc., Sunnyvale, Calif.) was used to determine light emission from cell extracts.

In Vitro Proliferation and Apoptosis Assays—

$5.10^3$ PC-3 or LNCaP cells were cultured in 96-well flat-bottomed tissue culture plates [Corning Incorporated, Corning, N.Y.]. After 24 h, wells were supplemented with fresh media, 200 µg/ml neutralizing anti-human MCP-1 antibodies, or 200 µg/ml total IgG from preimmune rabbits. Cells were cultured in the presence of the above at 37° C. in humidified air containing 7.5% $CO_2$. Respective media and additives were replaced every 5 days. After 5 days, each well was pulsed with 2 µCi of [$^3$H]-thymidine (specific activity 10 Ci/mmol) for 16 hours. The cultures were then harvested on fiberglass filters. Results are shown as mean CPM of six replicates ±SE from 3 independent experiments, divided by the mean CPM of control cells. Lysates of LNCaP and PC-3 cell lines were subjected to western blot analysis with anti-Active Caspase-3 (MBL Internation, Woburn, Mass.) as a primary Ab, to evaluate Apoptosis of these cell lines after treatment with anti-human MCP-1 Abs.

Purification of Neutralizing Rabbit Polyclonal Anti-Human MCP-1 Abs—

Single immunization of two rabbits with 500 µg of recombinant human MCP-1 in CFA (Complete Freund's Adjuvant) followed by 5 boosts with 250 µg protein in IFA were effected subcutaneously every 3 weeks. One week following the last boost, sera were collected for titer and affinity determination by a direct ELISA test. A High-Trap Protein G column (Pharmacia, Piscataway, N.J.) was used (according to the manufacturer's protocol) to purify the IgG fraction after binding. Purified IgG was then dialyzed in PBS and tested for specificity by Western Blot using different chemokines, as described above, and for their in vitro neutralizing characteristics using a TransWell system (Corning Costar Corporation, Cambridge, Mass.).

Evaluation of Anti-MCP-1 Ab Titer in Sera of CaP Patients and Sera of Rabbits—

A direct ELISA assay was used to determine anti-MCP-1 Ab titer in CaP patients. ELISA plates (Nunc, Roskilde, Denmark) were coated with 50 ng/well commercially available human MCP-1 (PeproTech, Rocky Hill, N.J.). Sera from patients were added in serial dilutions from $2^5$ to $2^{16}$ to wells that were, or were not, coated previously with rMCP-1. Calculation of each titer was effected by comparing the OD measured in wells coated with MCP-1 with those not coated with this recombinant chemokine. Secondary biotin-SP conjugated goat anti-human antibodies (Jackson ImmunoResearch) and alkaline phosphatase-streptavidin (Zymed Laboratories, San Francisco, Calif.) were used for labeling. p-Nitrophenyl phosphate (Sigma Aldrich) was used as a soluble alkaline phosphatase substrate. Results of triplicates were calculated as $log_2$ Ab titer ±SE. For determining rabbit anti human MCP-1 titer, biotin-SP conjugated goat anti-rabbit antibodies were used as a secondary antibody.

In Vitro Chemotaxis Assays—

THP-1 Chemotaxis assays were effected using a TransWell chamber (Corning Costar, Cambridge, Mass.). Medium suspended THP-1 cells ($1 \times 10^6$ cells/well) were added to the inside of the Transwell, after equilibration of the lower chambers with medium, 200 ng/ml human MCP-1 or chemokine with 200 µg/ml rabbit polyclonal anti MCP-1 antibodies, for ½ hour. Transwells were then incubated for 3 h at 37° C. in humidified air containing 7.5% $CO_2$. After incubation, monocytes which had migrated through the membrane to the lower chamber were collected and viable cells confirmed by trypan blue exclusion counted from 6 different fields at a magnification of ×400 by light microscopy. To test CaP cell lines LNCaP and PC-3 migration towards MCP-1 a Boyden chamber system was used. Same contents of wells as described above were used, with 8 µm pores membranes (Osmonics, Livermore, Calif.). After incubation, membranes were dyed using Diff-Quik (Dade Behring, Switzerland), and cells were counted from 6 different fields at a magnification of ×400, using light microscopy. Results are shown as mean of four independent experiments ±SE, divided by the mean cell counts of control cells. Membranes from LNCaP-GFP chemotaxis assays (obtained from the Boyden Chamber) were also filmed using fluorescence microscopy.

Structural Analysis of Cells—

PC-3 cells morphological changes were evaluated under the influence of recombinant MCP-1. PC-3 cells attached to plastic plate were exposed to an excessive concentration of the chemokine under different conditions, and photographed in 1-minute intervals for a total of 1 hour under light microscopy. The effects of a Medium containing anti-MCP-1 Abs in addition to recombinant MCP-1 or pretreatment of cells with Wortmannin (Sigma Aldrich)-a PI-3 kinase inhibitor on the morphology of PC-3 cells were tested similarly.

Statistical Analysis—

Significance of differences was examined using Student t test. P values less than 0.05 were considered significant.

Example 1

Selective Autoantibody Production to MCP-1, Participates in the Regulation of Prostate Cancer (CaP)

Human sera from 23 prostate cancer patients, 21 individuals with benign hypertrophy of the prostate (BPH) and 11 control subjects were tested for possible production of autoantibodies to various chemokines, particularly those that have been implicated with cancer diseases including: SDF-1 (CXCL12), MIF, MIP-1α (CCL3), MIP-1β (CCL4), IL-8 (CXCL8), IP-10 (CXCL10), MIP-3α (CCL20), MIP-3β (CCL-19), Lymphotactin (XCL1), MIG (CXCL9), RANTES (CCL5), MCP-3 (CCL7) and MCP-1 (CCL2). Among these chemokines, patients suffering from CaP developed a highly significant antibody titer exclusively to one of the above chemokines, MCP-1 (FIG. 1a, log Ab titer of 11.85±0.8). The baseline titer ($log_2$) of healthy individuals and of BPH patients to MCP-1, and also to each of the other examined gene products was 5-6 (data not shown). Thus, CaP patients develop a highly specific and selective antibody titer to MCP-1 (FIG. 1a, p<0.01). Analysis of the titer developed in different individuals (FIG. 1b) showed that about 82% of CaP patients (19/23) and only about 4.7% (1/21) of those with non-malignant prostate hyperplasia displayed a significant (log 2Ab titer >10, p<0.01) response to MCP-1. These results suggested a role for MCP-1 in the regulation of CaP.

Example 2

MCP-1 is Highly Expressed at Different Pathological Grades of Human Cancer of the Prostate (CaP)

The expression pattern of MCP-1 in malignant tumors from CaP patients at different stages of disease was examined. The Gleason grading is used by pathologists to determine the aggressiveness of prostate cancer by microscopic examination of a biopsy specimen taken from the organ. The Gleason system is based on the architecture and differentiation rate of the prostatic gland cells, and ranges from 1 (very well differentiated) to 5 (very poorly differentiated). The Gleason score is usually given as the sum of Gleason grade for the two most common patterns of an examined prostate gland. FIGS. 2a-c show representative sections from patients at different stage of disease. The different stages of the disease are shown in FIGS. 2a-c, wherein FIG. 2a shows a prostate gland of a patient with hyperplasia of the prostatic glands (BPH) with a level of prostate serum antigen (PSA) of PSA=5.2; FIG. 2b shows a sample of adenocarcinoma of the prostate Gleason 6(3+3) (i.e., intermediate stage) PSA=7.4, and FIG. 2c from a patient with severe CaP, Gleason 9(4+5) (high grade) PSA=68. Immunostaining of these samples (FIGS. 2d-f, respectively) showed that not only the tumor cells, but also smooth muscle cells of the stroma surrounding glandular areas were intensively stained with anti MCP-1 antibodies. Interestingly, intensity of MCP-1 staining was correlated with cancer grade.

To determine the expression level of MCP-1 in cell-lines of androgen-dependent stage of prostate cancer (LNCaP) and androgen-independent stage (PC-3, DU-145) of prostate cancer, an RT-PCR analysis was effected. As is shown in FIG. 2g, all lines expressed MCP-1, regardless of hormonal dependency. The secretion of MCP-1 was also verified by ELISA assay (not show). Surprisingly each of these cell lines was found to express the receptor of MCP-1, CCR2 (FACS analysis, not shown).

Altogether these findings, together with the above, suggest that MCP-1 could play a role, in the development and progression of CaP. The experiments described bellow were conducted to delineate this role.

Example 3

MCP-1 Induces Chemotactic Migration and Morphological Changes in Human CaP Cell Lines, Via a G-Coupled Receptor The finding that CCR2 is expressed on prostate cancer cells suggested that MCP-1, produced by malignant cells and by smooth muscle cells of the stroma surrounding glandular areas (FIG. 2) may function as a chemoattractant for such cancer cells.

To test this, human MCP-1 was cloned from PC-3 cells, and polyclonal anti-human MCP-1 Abs were generated in rabbits. The specificity of these antibodies to MCP-1 was then examined by Western blot analysis. As is shown in FIG. 3a lower pannel, these antibodies bound MCP-1, but did not bind lymphotactin (XCL1), MIP-1α (CCL3), RANTES (CCL5), MCP-3 (CCL7), MIP-3β (CCL19), MIP-3α (CCL20), IL-8 (CXCL8), MIG (CXCL9), IP-10 (CXCL10) or SDF-1 (CXCL12). Expression of the above-indicated cytikines is shown in FIG. 3a upper panel.

The migration neutralization ability of these antibodies was evaluated in vitro in a Trans-Well system using THP-1 cell line as target cells (data not shown). Additionally, prostate cell lines were incubated in a Boyden chamber system in the presence or absence of the chemokine. As is shown in FIGS. 3b-c, both LNCaP and PC-3 cells lines transmigrated towards human MCP-1. This migration could then be significantly blocked by the above generated, and commercially available (not shown) neutralizing antibodies to MCP-1 (FIG. 3b).

A series of time-laps experiments using light microscopy showed an immediate response (i.e., plasma membrane protrusions, probably due to actin filament polymerization) of PC-3 cells attached to plastic surface, when exposed to an excessive concentration of recombinant MCP-1 in the medium (FIG. 3d, panels a-c, arrows). These results may provide a morphological explanation to the mechanistic basis of cell movement due to pseudopodia formation. Addition of anti-MCP-1 Ab (FIG. 3d, panels d-f) or pretreatment of cells with Wortmannin, a PI-3 kinase inhibitor (FIG. 3d, panels g-i), abolished this effect, suggesting that MCP-1 induces chemotaxis of adenocarcinoma cells of the prostate, via a G-coupled receptor, probably, CCR2.

Example 4

MCP-1 is an Autocrine Survival Factor of Human CaP Cell Lines

The effect of the above-generated anti-MCP-1 neutralizing antibody on prostate cancer cell proliferation was determined by [$^3$H]-Thymidine uptake. As is shown in FIG. 4a, LNCaP and PC-3 cells cultured in the presence of anti-MCP-1 Abs showed a significantly lower proliferation rate compared to cells treated with control IgG from pre-immunized rabbits (i.e., proliferation rates of LNCaP and PC-3 cells in the presence of MCP-1 neutralizing antibodies were 5.84%±0.7% and 35.24%±3.8%, respectively, and in the presence of control IgG from pre-immunized rabbits were 75.91%±7.6% and 80.75%±9%, respectively, p<0.001). This implies that MCP-1 can serve as a growth factor, a survival factor, or both, for prostate cell lines. It was then suggested that as a potential survival factor MCP-1 might be required to prevent apoptosis of cancer cells. It is well established that active Caspase-3a is indicative of an apoptotic process. For this reason, anti active Caspase-3 Abs were used to determine if this proteolytic enzyme is activated in LNCaP and PC-3 cells cultured as described above. As is shown in FIG. 4b, Caspase-3 expression was selectively elevated in wells enriched with anti MCP-1, but not control, antibodies.

Example 5

Figure 5B:
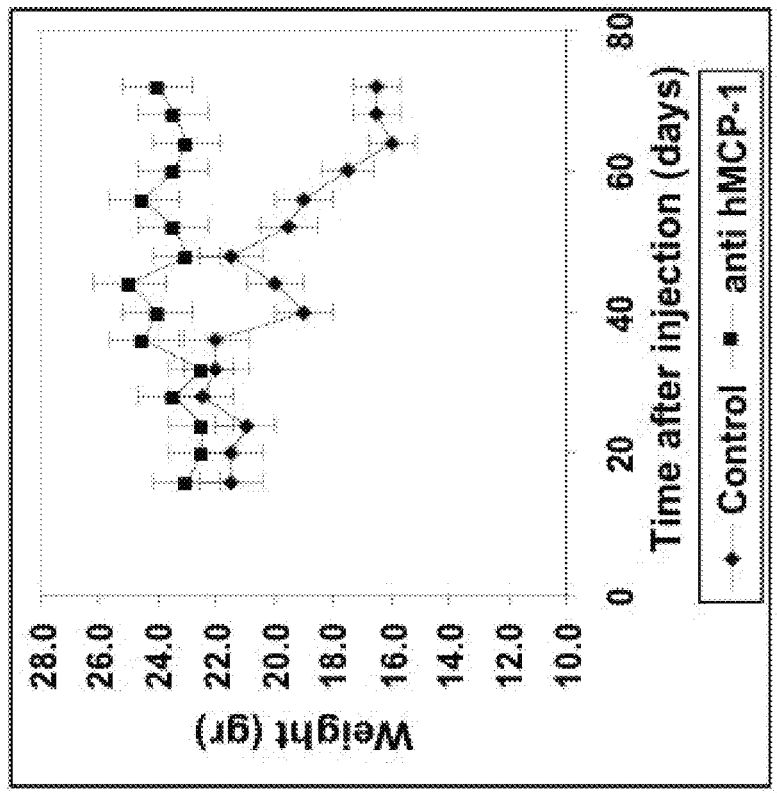

Neutralization of MCP-1 Prevents Tumor Progression In Vivo in LNCaP/SCID Mouse Model The above findings may imply for a possible role for MCP-1 in the regulation of CaP. To explore this possibility a group of SCID/Bj mice was injected with LNCaP cells ($8 \times 10^6$ S.C.). Four days later mice were randomly separated to two subgroups that were repeatedly (in a four days interval) administered with either rabbit anti human MCP-1 antibodies (described above) or with control IgG from pre-immunized rabbits. Tumor volume was calculated (FIG. 5b), and total weight of mice was also recorded (FIG. 5a). As is shown in FIG. 5b, control mice developed tumor volumes of up to $1370 \pm 270$ mm$^3$. In addition, these control mice showed failure to thrive by day 65 and survived only $76 \pm 5.2$ days. In contrast, those treated with anti MCP-1 antibodies did not show any signs of physical distress, and did not develop tumors. Hence, anti MCP-1 treatment completely abolished the tumorigenic effects of LNCaP (FIGS. 5a-b).

Example 6

Neutralization of MCP-1 Suppresses PC-3 Induced Tumor Progression

The non-androgen dependent PC-3 cell line is a more aggressive cell line than the androgen dependent LNCaP. Since it was found that CCR2 expressing PC-3 cells are attracted by MCP-1 and undergo apoptosis in its absence of MCP-1 gene product (FIG. 3a), the effects of MCP-1 neutralization on the development PC-3 tumors in vivo was examined. Again, a group of SCID/Bj mice was inoculated with PC-3 cells ($5 \times 10^6$, S.C.) subcutaneously. Four days later, mice were randomly separated to two subgroups that were repeatedly (in a four day interval) administered with either our rabbit anti human MCP-1 antibodies or with control IgG from pre-immunized rabbits. Tumor volume was calculated and total weight of mice was also recorded. As is shown in FIG. 6a, control mice developed aggressive tumors and failed to thrive by day 46 and survived only $58 \pm 4$ days. In contrast, 33% (2/6) of those treated with anti MCP-1 antibodies never showed any sign of physical distress, and the other four survived more then 80 days, and developed smaller tumors more slowly (FIG. 6a).

In order to assess the effects of MCP-1 neutralization on PC-3 tumors, another experiment conducted under the same conditions was effected, only mice were sacrificed 60 days after the beginning of the experiment. Once again, neutralization of MCP-1 suppressed the development and progression of the tumor. The subcutaneous primary tumor of a representative control mouse (FIG. 6b, panel a), and area of cancer cell inoculation of a treated mouse (FIG. 6b, panel b) clearly showed the difference between the two groups. Prior to being sacrificed these mice were also subjected to X-Ray image analysis. While control mouse (FIG. 6b, panel c) revealed large subcutaneous metastase adjacent to the neck (left arrow) in addition to the primary tumor (right arrow), there was no trace of tumor in the treated mouse (FIG. 6b, panel d).

Thereafter, the expression of MCP-1 and its receptor, CCR2, in tumor tissues dissected from the mice was determined. Immunohistochemistry showed vast expression of MCP-1 (FIG. 6c, panel a) and its receptor, CCR2 (FIG. 6c, panel b), on the tumor cells. Sections from tissue samples of both groups, were also subjected them to immunostaining analysis with anti-CD11b mAb, a cell-surface marker of mouse macrophages. As is evident from FIG. 6d, panel a, Tumor-associated Macrophages (TAM's) were seen close to the tumor margins in an untreated control mouse, however no TAM's were observed in a tumor from treated mouse (FIG. 6d, panel b).

It is possible that TAM's are important to the tumor angiogenesis since they produce and secrete angiogenic factors required for the invasion of the tumor. Indeed, immunostaining of these sections with platelet-endothelial cell adhesion molecule-1 (PECAM-1, CD31), an endothelial marker clearly showed that control mice (FIG. 6e, panels a-b) displayed a significantly higher ($p<0.01$, FIG. 6e, panel d) number of blood vessels in tumors compared to those previously treated with anti MCP-1 Abs (FIG. 6e, panel c).

Example 7

Anti CCR2 Antibodies and Their Inhibitory Effect on Prostate Cell Proliferation

Figure 7:
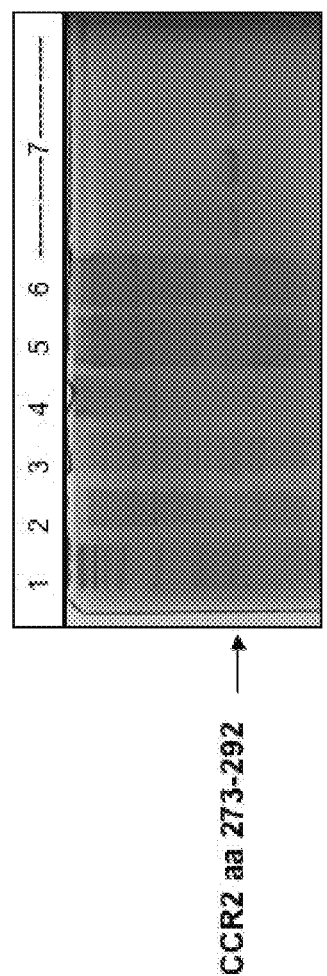
FIG. 7 is a photograph depicting the production of a recombinant polypeptides consisting of the third extracellular domain of human CCR2 (3D-CCR2). The third extracellular domain of human CCR2 (3D-CCR2, amino acids 273-292) was cloned from LNCaP cells cDNA (using an RT-PCR reaction) into pET30a expression vector, and over expressed in *E. coli* BL21. Lanes from left to right: 1. Protein Marker; 2. Non-induced lysate; 3. IPTG-Induced lysate; 4. culture supernatant before induction; 5. bacterial pellet after induction; 6. culture supernatant after binding to a Nickel column; 7. an eluate of the recombinant protein.

Materials and Experimental Procedures
Generation of Antibodies
Production of Recombinant Human CCR2 (rCCR2)—
Reverse transcriptase reaction (RT) was applied on LNCaP human cell line using Oligonucleotide primers specific to human CCR2 (5'-ATGCTGTCCACATCTCGTTCTC-3' and 5'-CCAACCAGGTGATCACACTTGT-3', SEQ ID NOs: 14 and 15, respectively) that were designed based on the published CCR2 nucleic acid sequence (GenBank Accession NO. NM_000647). The amplification conditions were: 25 PCR cycles, with a thermal cycle profile of denaturation for 1 min at 95° C., annealing for 1 min at 55° C., and extension for 1 min at 72° C. After PCR reaction, the mixtures were loaded onto a 5% polyacrylamide gel in TAE buffer. Relevant RT-PCR reactions showed specific bands. PCR product was then cloned and the appropriate sequence was verified. RT-PCR reaction was then applied, once again, using specific oligonucleotide primers for amplifying the extracellular domain of human CCR2 (amino acids 273-292), containing cleavage sites for BamHI-EcoRI (5'(BamHI)-CGCGGATCCGGCCT-GAGTAACTGTGAAAGAATGC-3', and 5'-CCGGAAT-TCAGTCTCTGTCACCTGCGTGG-3'(EcoRI), SEQ ID NOs: 16 and 17, respectively (FIG. 7). PCR products were then cleaved with restriction enzymes (BamHI, EcoRI), cloned into pET-30a and transformed to *Escherichia coli*. Sequence was verified.

Figure 8:
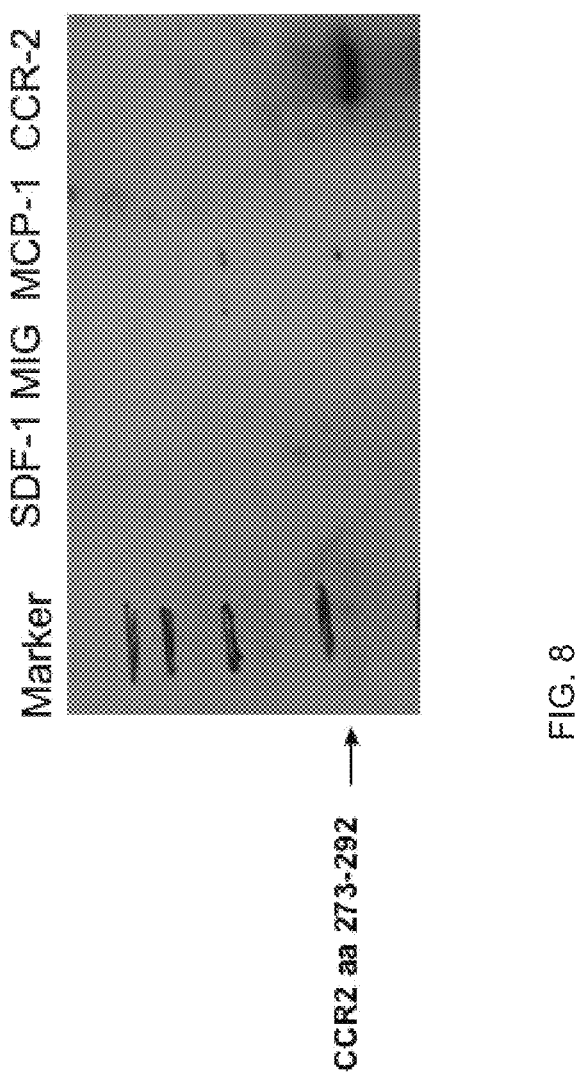
FIG. 8 is a photograph depicting the specificity of rabbit polyclonal anti-CCR2 Abs of the present invention as determined by Western Blot analysis. Recombinant CCR2 (third extracellular domain), and additional 3 chemokines (MCP-1, SDF-1, MIG), were SDS resolved and transferred to a nitrocellulose membrane. The membrane was incubated with rabbit polyclonal anti-CCR2Abs, followed by an ECL reaction.

Production and Purification of rCCR2 (aa 273-292)—
The above PCR product was expressed in *E. coli* and then purified by an NI-NTA-supper flow affinity purification of 6×His proteins (Qiagen, Chatsworth, Calif.). After purification, the purity of rCCR2 (aa 273-292) was verified by gel electrophoresis, by Western blot, and by sequencing (FIG. 8).

Production and Purification of Neutralizing Rabbit Polyclonal Anti-Human CCR2 (aa 273-292) Abs—
Single immunization of two rabbits with 500 µg of recombinant human CCR2 (aa 273-292) in CFA (Complete Freund's Adjuvant Difco laboratories, Inc., Detroit, Mich.), followed by 5 boosts with 250 µg protein in IFA (Incomplete Freund's adjuvant, Difco) subcutaneously was given to rabbits every 3 weeks. One week following the last boost, sera were collected for titer and affinity determination by a direct ELISA test. A High-Trap Protein G column (Pharmacia, Piscataway, N.J.) was used to purify the IgG fraction after biding. Purified IgG was then dialyzed in PBS and tested for specificity by Western Bloting.

Results

Anti CCR-2 Antibodies Block the Growth of the Androgen Independent PC3 Human Prostate Cancer Cell Line—

Figure 9:
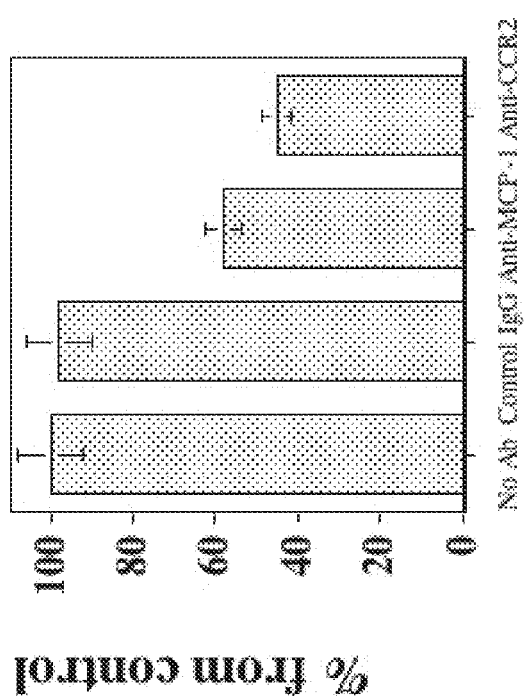
FIG. 9 is a bar graph depicting the ability of anti CCR-2 antibodies to block the growth of androgen independent PC3 human prostate cancer cell line. 5000 PC-3 cells or LNCaP cells were cultured in 96-well flat-bottomed tissue culture plates in the presence of an anti-MCP-1 neutralizing antibodies (200 µg/ml), anti CCR-2 antibodies, or total IgG from pre-immunized rabbits, for 5 days. Proliferation rates were estimated using a [$^3$H]-Thymidine assay. The figure summarizes results from triplicates as % from control ±SE.

PC-3 cells were cultured in the presence of the above-described anti-MCP-1 neutralizing antibodies (200 µg/ml) or anti the anti-CCR-2 antibodies, or total IgG from pre-immunized rabbits, for 5 days. Thereafter, proliferation rates were estimated using a [$^3$H]-Thymidine assay (FIG. 9). Proliferation rates of cells cultured with either anti-MCP-1 antibodies or anti CCR-2 antibodies were significantly lower than control antibodies ($p<0.001$). This substantiates the important role of MCP-1 as a growth factor for the androgen independent stage of prostate cancer and suggests anti MCP-1 and anti CCR-2 antibody administrations as a therapeutic approach for prostate cancer.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED BY NUMERALS

Additional References are Cited in the Text

1. Zlotnic, A. & Yoshei, O. Chemokines: A new classification system and their role in immunity. *Immunity* 12, 121-127 (2000).
2. Wildbaum, G., Nahir, M. & Karin, N. Beneficial autoimmunity to proinflammatory mediators restrains the consequences of self-destructive immunity. *Immunity* 19, 679-688 (2003).
3. Wildbaum, G., Netzer, N. & Karin, N. Plasmid DNA encoding IFN-gamma-inducible protein 10 redirects antigen-specific T cell polarization and suppresses experimental autoimmune encephalomyelitis. *J Immunol* 168, 5885-92. (2002).
4. Wildbaum, G., Westermann, J., Maor, G. & Karin, N. A targeted DNA vaccine encoding fas ligand defines its dual role in the regulation of experimental autoimmune encephalomyelitis. *J Clin Invest* 106, 671-9. (2000).
5. Wildbaum, G. & Karin, N. Augmentation of natural immunity to a pro-inflammatory cytokine (TNF-alpha) by targeted DNA vaccine confers long-lasting resistance to experimental autoimmune encephalomyelitis. *Gene Ther* 6, 1128-38. (1999).
6. Salomon, I. et al. Targeting the Function of IFN-gamma-Inducible Protein 10 Suppresses Ongoing Adjuvant Arthritis. *J Immunol* 169, 2685-93. (2002).
7. Blank, M., Krause, I., Wildbaum, G., Karin, N. & Shoenfeld, Y. TNFalpha DNA vaccination prevents clinical manifestations of experimental antiphospholipid syndrome. *Lupus* 12, 546-9 (2003).
8. Youssef, S. et al. C—C chemokine-encoding DNA vaccines enhance breakdown of tolerance to their gene products and treat ongoing adjuvant arthritis. *J Clin Invest* 106, 361-71. (2000).
9. Youssef, S. et al. Long-lasting protective immunity to experimental autoimmune encephalomyelitis following vaccination with naked DNA encoding C—C chemokines. *J Immunol* 161, 3870-9. (1998).
10. Muller, A. et al. Involvement of chemokine receptors in breast cancer metastasis. *Nature* 410, 50-6. (2001).
11. Homey, B., Muller, A. & Zlotnik, A. Chemokines: agents for the immunotherapy of cancer? *Nature Rev Immunol* 2, 175-84. (2002).
12. Murphy, P. M. Chemokines and the molecular basis of cancer metastasis. *N Engl J Med* 345, 833-5. (2001).
13. Strieter, R. M. et al. The functional role of the ELR motif in CXC chemokine-mediated angiogenesis. *J Biol Chem* 270, 27348-57. (1995).
14. Arenberg, D. A. et al. The role of CXC chemokines in the regulation of angiogenesis in non-small cell lung cancer. *J Leukoc Biol* 62, 554-62. (1997).
15. Belperio, J. A. et al. CXC chemokines in angiogenesis. *J Leukoc Biol* 68, 1-8. (2000).
16. Arenberg, D. A., White, E. S., Burdick, M. D., Strom, S. R. & Strieter, R. M. Improved survival in tumor-bearing SCID mice treated with interferon-gamma-inducible protein 10 (IP-10/CXCL10). *Cancer Immunol Immunother* 50, 533-8. (2001).
17. Rollins, B. J. Monocyte chemoattractant protein 1: a potential regulator of monocyte recruitment in inflammatory disease. *Mol Med Today* 2, 198-204 (1996).
18. Karpus, W. J. et al. An important role for the chemokine macrophage inflammatory protein-1 alpha in the pathogenesis of the T cell-mediated autoimmune disease, experimental autoimmune encephalomyelitis. *J Immunol* 155, 5003-10 (1995).
19. Izikson, L., Klein, R. S., Charo, I. F., Weiner, H. L. & Luster, A. D. Resistance to experimental autoimmune encephalomyelitis in mice lacking the CC chemokine receptor (CCR)2. *J Exp Med* 192, 1075-80. (2000).
20. Huang, D. R., Wang, J., Kivisakk, P., Rollins, B. J. & Ransohoff, R. M. Absence of monocyte chemoattractant protein 1 in mice leads to decreased local macrophage recruitment and antigen-specific T helper cell type 1 immune response in experimental autoimmune encephalomyelitis. *J Exp Med* 193, 713-26. (2001).

21. Gong, J. H., Ratkay, L. G., Waterfield, J. D. & Clark-Lewis, I. An antagonist of monocyte chemoattractant protein 1 (MCP-1) inhibits arthritis in the MRL-lpr mouse model. *J Exp Med* 186, 131-7 (1997).
22. Garnick, M. B. Prostate cancer: screening, diagnosis, and management. *Ann Intern Med* 118, 804-18. (1993).
23. Pienta, K. J. & Esper, P. S. Risk factors for prostate cancer. *Ann Intern Med* 118, 793-803. (1993).
24. Moore, B. B. et al. Distinct CXC chemokines mediate tumorigenicity of prostate cancer cells. *Am J Pathol* 154, 1503-12. (1999).
25. Ferrer, F. A. et al. Angiogenesis and prostate cancer: in vivo and in vitro expression of angiogenesis factors by prostate cancer cells. *Urology* 51, 161-7. (1998).
26. Inoue, K. et al. Interleukin 8 expression regulates tumorigenicity and metastases in androgen-independent prostate cancer. *Clin Cancer Res* 6, 2104-19. (2000).
27. Reiland, J., Furcht, L. T. & McCarthy, J. B. CXC-chemokines stimulate invasion and chemotaxis in prostate carcinoma cells through the CXCR2 receptor. *Prostate* 41, 78-88. (1999).
28. Kim, S. J. et al. Expression of interleukin-8 correlates with angiogenesis, tumorigenicity, and metastasis of human prostate cancer cells implanted orthotopically in nude mice. *Neoplasia* 3, 33-42. (2001).
29. Veltri, R. W. et al. Interleukin-8 serum levels in patients with benign prostatic hyperplasia and prostate cancer. *Urology* 53, 139-47. (1999).

What is claimed is:

1. A method of diagnosing presence of prostate cancer in a male subject, the method comprising:
    (a) determining a level of anti MCP-1 antibodies and a level of prostate specific antigen (PSA) or prostatic acid phosphatase (PAP) or both in a serum or plasma sample obtained from the subject;
    (b) comparing said level of anti MCP-1 antibodies and level of PSA or PAP or both in said serum or plasma sample with a level of anti MCP-1 antibodies and a level of PSA or PAP or both in serum or plasma samples from a population of normal healthy male controls, wherein an increase in the level of said anti MCP-1 antibodies and level of PSA or PAP or both in said serum or plasma sample of said subject above the level of said anti MCP-1 antibodies and level of PSA or PAP or both in said serum or plasma samples from said normal healthy male controls is indicative of the prostate cancer in the subject.

2. The method of claim 1, wherein said determining a level of said anti-MCP-1 antibodies in said serum or plasma sample is effected by immunohistochemistry, ELISA, RIA and/or Western blot analysis.

3. The method of claim 1, wherein when said comparing in (b) indicates increased anti MCP-1 antibody levels and increased levels of PSA or PAP or both in said sample of said subject, as compared to the levels from said normal healthy male controls, subjecting said subject having increased anti-MCP-1 antibody levels and level of PSA or PAP or both to a further diagnostic method for prostate cancer.

4. A method of determining a predisposition to prostate cancer in a male subject, the method comprising
    (a) determining a level of anti MCP-1 antibodies and a level of PSA or PAP or both in a serum or plasma sample obtained from the subject;
    (b) comparing said level of anti MCP-1 antibodies and a level of PSA or PAP or both in said serum or plasma sample with a level of anti MCP-1 antibodies and a level of PSA or PAP or both in serum or plasma samples from a population of normal healthy male controls, wherein an increase in the level of said anti MCP-1 antibodies and level of PSA or PAP or both in said serum or plasma sample of said male subject above the level of said anti-MCP-1 antibodies and level of PSA or PAP or both in said serum or plasma samples from said normal healthy male controls, is indicative of the predisposition to prostate cancer in the subject.

5. The method of claim 4, wherein said determining a level of said anti-MCP-1 antibodies in said serum or plasma sample is effected by immunohistochemistry, ELISA, RIA and/or Western blot analysis.

6. The method of claim 3, wherein said further diagnostic method is selected from the group consisting of trans rectal ultrasound (TRUS), CT-scan, bone scan, MRI and surgical biopsy.

7. The method of claim 1, comprising determining a level of anti MCP-1 antibodies and a level of PSA in a serum or plasma sample obtained from the subject, and comparing said level of anti MCP-1 antibodies and level of PSA in said serum or plasma sample with a level of anti MCP-1 antibodies and a level of PSA in serum or plasma samples from a population of normal healthy male controls, wherein an increase in the level of said anti MCP-1 antibodies and level of PSA in said serum or plasma sample of said subject above the level of said anti MCP-1 antibodies and level of PSA in said serum or plasma samples from said normal healthy male controls is indicative of the prostate cancer in the subject.

8. The method of claim 4, comprising determining a level of anti MCP-1 antibodies and a level of PSA in a serum or plasma sample obtained from the subject, and comparing said level of anti MCP-1 antibodies and level of PSA in said serum or plasma sample with a level of anti MCP-1 antibodies and a level of PSA in serum or plasma samples from a population of normal healthy male controls, wherein an increase in the level of said anti MCP-1 antibodies and level of PSA in said serum or plasma sample of said subject above the level of said anti MCP-1 antibodies and level of PSA in said serum or plasma samples from said normal healthy male controls is indicative of predisposition to prostate cancer in the subject.

9. A method of monitoring disease progression in a prostate cancer patient, the method comprising:
    (a) determining a level of anti MCP-1 antibodies in a serum or plasma sample obtained from the patient;
    (b) comparing said level of anti MCP-1 antibodies in said serum or plasma sample with a level of anti MCP-1 antibodies in an earlier serum or plasma sample from said patient, wherein a level of anti MCP-1 antibodies above the level of said anti MCP-1 antibodies in said earlier sample is indicative of progressive prostate cancer in the patient.

10. The method of claim 9, further comprising determining levels of PSA or PAP or both in said sample of said patient.

11. The method of claim 9, wherein said determining a level of said anti-MCP-1 antibodies in said serum or plasma sample is effected by immunohistochemistry, ELISA, RIA and/or Western blot analysis.

* * * * *

SEQUENCE LISTING

```
<160> NUMBER OF SEQ ID NOS: 17

<210> SEQ ID NO 1
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 1
atgaaagtct ctgccgccct tc                                              22

<210> SEQ ID NO 2
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 2
tcaagtcttc ggagtttggg tt                                              22

<210> SEQ ID NO 3
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 3
atgctgtcca catctcgttc tc                                              22

<210> SEQ ID NO 4
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 4
ccaaccaggt gatcacactt gt                                              22

<210> SEQ ID NO 5
<211> LENGTH: 29
<212> TYPE: DNA
<213> ORGANISM: Artificial sequence
<220> FEATURE:
<223> OTHER INFORMATION: Single strand DNA oligonucleotide
```

```
<400> SEQUENCE: 5
gctgatatcc agccagatgc aatcaatgc                                    29

<210> SEQ ID NO 6
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 6
ccggaattct caagtcttcg gagtttggg                                    29

<210> SEQ ID NO 7
<211> LENGTH: 231
<212> TYPE: DNA
<213> ORGANISM: Artificial sequence
<220> FEATURE:
<223> OTHER INFORMATION: PCR product incoding human rMCP-1

<400> SEQUENCE: 7
cagccagatg caatcaatgc cccagtcacc tgctgttata acttcaccaa taggaagatc    60
tcagtgcaga ggctcgcgag ctatagaaga atcaccagca gcaagtgtcc caaagaagct   120
gtgatcttca agaccattgt ggccaaggag atctgtgctg accccaagca gaagtgggtt   180
caggattcca tggaccacct ggacaagcaa acccaaactc cgaagacttg a            231

<210> SEQ ID NO 8
<211> LENGTH: 76
<212> TYPE: PRT
<213> ORGANISM: Artificial sequence
<220> FEATURE:
<223> OTHER INFORMATION: Translated human rMCP-1

<400> SEQUENCE: 8

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75

<210> SEQ ID NO 9
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 9
atgaaagtct ctgccgccct tc                                           22

<210> SEQ ID NO 10
<211> LENGTH: 22
<212> TYPE: DNA
<213> ORGANISM: Artificial sequence
<220> FEATURE:
<223> OTHER INFORMATION: Single strand DNA oligonucleotide
```

-continued

<400> SEQUENCE: 10
tcaagtcttc ggagtttggg tt                                                22

<210> SEQ ID NO 11
<211> LENGTH: 207
<212> TYPE: DNA
<213> ORGANISM: Artificial sequence
<220> FEATURE:
<223> OTHER INFORMATION: Truncated hMCP-1 nucleotide sequence

<400> SEQUENCE: 11
gtcacctgct gttataactt caccaatagg aagatctcag tgcagaggct cgcgagctat      60
agaagaatca ccagcagcaa gtgtcccaaa gaagctgtga tcttcaagac cattgtggcc     120
aaggagatct gtgctgaccc caagcagaag tgggttcagg attccatgga ccacctggac     180
aagcaaaccc aaactccgaa gacttga                                         207

<210> SEQ ID NO 12
<211> LENGTH: 68
<212> TYPE: PRT
<213> ORGANISM: Artificial sequence
<220> FEATURE:
<223> OTHER INFORMATION: Truncated hMCP-1 protein sequence

<400> SEQUENCE: 12

Val Thr Cys Cys Tyr Asn Phe Thr Asn Arg Lys Ile Ser Val Gln Arg
1               5                   10                  15

Leu Ala Ser Tyr Arg Arg Ile Thr Ser Ser Lys Cys Pro Lys Glu Ala
            20                  25                  30

Val Ile Phe Lys Thr Ile Val Ala Lys Glu Ile Cys Ala Asp Pro Lys
        35                  40                  45

Gln Lys Trp Val Gln Asp Ser Met Asp His Leu Asp Lys Gln Thr Gln
    50                  55                  60

Thr Pro Lys Thr
65

<210> SEQ ID NO 13
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 13
cgcggatccg tcacctgctg ttataactt                                       29

<210> SEQ ID NO 14
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 14
atgctgtcca catctcgttc tc                                              22

<210> SEQ ID NO 15
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 15

```
ccaaccaggt gatcacactt gt                                               22

<210> SEQ ID NO 16
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 16
cgcggatccg gcctgagtaa ctgtgaaaga atgc                                  34

<210> SEQ ID NO 17
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 17
ccggaattca gtctctgtca cctgcgtgg                                        29
```